(12) United States Patent
Wu et al.

(10) Patent No.: US 7,214,691 B2
(45) Date of Patent: May 8, 2007

(54) 2-SUBSTITUTED BENZIMIDAZOLE DERIVATIVES AS SELECTIVE MELANIN CONCENTRATING HORMONE RECEPTOR ANTAGONISTS FOR THE TREATMENT OF OBESITY AND RELATED DISORDERS

(75) Inventors: Wen-Lian Wu, Edison, NJ (US); Duane A. Burnett, Bernardsville, NJ (US); Mary Ann Caplen, Sayreville, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/924,070

(22) Filed: Aug. 23, 2004

(65) Prior Publication Data
US 2005/0049269 A1 Mar. 3, 2005

Related U.S. Application Data

(60) Provisional application No. 60/532,333, filed on Dec. 23, 2003, provisional application No. 60/497,837, filed on Aug. 25, 2003.

(51) Int. Cl.
*A61K 31/454* (2006.01)
*C07D 401/06* (2006.01)

(52) U.S. Cl. ............ 514/322; 546/199; 546/198; 546/194; 546/16; 514/321; 514/318; 514/278

(58) Field of Classification Search ............ 514/322, 514/321, 318, 278; 546/199, 198, 194, 16
See application file for complete search history.

(56) References Cited

U.S. PATENT DOCUMENTS 5,674,866 A * 10/1997 Janssens et al. ....... 514/214.02
5,908,830 A      6/1999 Smith et al.

FOREIGN PATENT DOCUMENTS

WO    WO 02/076947    10/2002
WO    WO 03/044023    5/2003
WO    WO 03/060475    7/2003
WO    WO 03/088908    10/2003

OTHER PUBLICATIONS

International Search Report for PCT/US2004/027240 (CN06099US01) - 5 Pages.
Shamada et al., Mice lacking melanin-concentrating hormone are hypophagic and lean, Nature, vol. 396 (Dec. 17, 1998) 670-674.
Shanklin Jr., et al., Synthesis Calcium-Channel-Blocking Acitivity . . . , Journal of Med. Chem. American Chem. Society, 34:10 (1991) 3011-3022 XP002241320.
Burckhalter, J. H. et al., 2-(2-pYRIDYL)-1,2-diarylalkanols as hypocholesteremic agents, Journal of Med. Chem. American Chem. Society 10:4 (Jul. 1967) 565-575 XP002904134.
Beth Borowsky et al., Antidepressant, anxiolytic and anorectic effects. . Nature Medicine, 8:8 (Aug. 2002) 825-830.

* cited by examiner

*Primary Examiner*—Charanjit S. Aulakh
(74) *Attorney, Agent, or Firm*—William Y. Lee

(57) ABSTRACT

The present invention discloses compounds of formula I

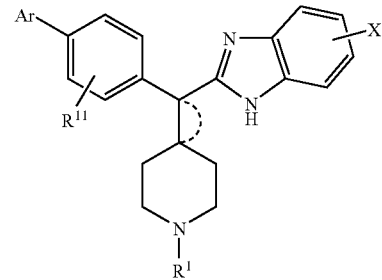

wherein Ar, X, $R^1$ and $R^{11}$ are herein defined, said compounds being novel antagonists for melanin-concentrating hormone (MCH), as well as methods for preparing such compounds. In another embodiment, the invention discloses pharmaceutical compositions comprising such MCH antagonists as well as methods of using them to treat obesity, metabolic disorders, eating disorders such as hyperphagia, and diabetes.

25 Claims, No Drawings

2-SUBSTITUTED BENZIMIDAZOLE DERIVATIVES AS SELECTIVE MELANIN CONCENTRATING HORMONE RECEPTOR ANTAGONISTS FOR THE TREATMENT OF OBESITY AND RELATED DISORDERS

CROSS REFERENCE TO RELATED APPLICATION

This application claims the benefit of U.S. Provisional Application 60/497,837 filed Aug. 25, 2003 and U.S. Provisional Application 60/532,333 filed Dec. 23, 2003.

FIELD OF THE INVENTION

This invention relates to antagonists for melanin-concentrating hormone (MCH) and their use in the treatment of metabolic and eating disorders, novel compounds having MCH receptor modulatory activity, pharmaceutical compositions containing one or more such modulators, methods of preparing such modulators and methods of using such modulators to treat obesity, diabetes and related disorders.

BACKGROUND OF THE INVENTION

MCH, a cyclic peptide, was first identified over a decade ago in teleost fish where it appears to regulate color change. More recently, MCH has been the subject of investigation for its possible role as a regulator of eating behavior in mammals. As reported by Shimada et al., Nature, Vol. 396 (17 Dec. 1998), pp. 670–673, MCH-deficient mice have reduced body weight and leanness due to hypophagia (reduced feeding). In view of their findings, it was suggested that antagonists of MCH may be effective for the treatment of obesity. U.S. Pat. No. 5,908,830 discloses a combination therapy for the treatment of diabetes or obesity involving the administration of a metabolic rate increasing agent and a feeding behavior modifying agent, an example of the latter being an MCH antagonist. Further, MCH receptor antagonists may also be useful in the treatment of depression and/or anxiety. Borowksy et al., Nature Medicine, 8, pp. 825–830 (1 Aug. 2002).

SUMMARY OF THE INVENTION

In one embodiment, this invention provides novel biaryl-piperidine-4-ylidene-methyl benzimidazole derivative compounds having MCH antagonist activity. These compounds are represented by formula I or a pharmaceutically acceptable salt or solvate thereof, wherein the dashed line of along with the adjoining single bond, together represent a double bond, a cyclopropyl or cyclobutyl;

Ar is aryl, heteroaryl, $R^4$-substituted aryl or $R^4$-substituted heteroaryl;

$R^1$ is hydrogen, alkyl, aralkyl, aryl, cycloalkyl, cycloalkylalkyl, heteroaralkyl, heteroaryl, $R^4$-substituted aralkyl, $R^4$-substituted aryl, $R^4$-substituted cycloalkyl, $R^4$-substituted cycloalkylalkyl, $R^4$-substituted heteroaralkyl, $R^4$-substituted heteroaryl, -alkylenyl-C(O)$R^8$, —C(O)$R^2$, —S(O$_2$)$R^7$, —S(O$_2$)NR$^2$R$^3$, —C(O)NR$^2$R$^3$ or —C(O)OR$^7$;

$R^2$ is hydrogen, heteroaryl, alkyl or aryl;

$R^3$ is hydrogen, heteroaryl, alkyl or aryl, where $R^2$ and $R^3$ can be optionally joined together and with the nitrogen to which they are attached, form a heterocyclyl ring, wherein said heterocyclyl ring can be optionally substituted with a ring system substituent, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halogen, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), $Y_1Y_2N$—, $Y_1Y_2N$-alkyl-, $Y_1Y_2NC(O)$—, $Y_1Y_2NSO_2$— and —SO$_2$NY$_1$Y$_2$, wherein $Y_1$ and $Y_2$ can be the same or different and are independently selected from the group consisting of hydrogen, alkyl, aryl, cycloalkyl, and aralkyl;

$R^4$ is 1 to 5 moieties and each $R^4$ is independently selected from group the consisting of hydrogen, heterocyclyl, $R^8$-substituted heterocyclyl, heterocyclylalkyl, $R^8$-substituted heterocyclylalkyl, aryl, cycloalkyl, cycloalkylalkyl, heteroaralkyl, heteroaryl, $R^8$-substituted aryl, $R^8$-substituted cycloalkyl, $R^8$-substituted cycloalkylalkyl, $R^8$-substituted heteroaralkyl, $R^8$-substituted heteroaryl, —OH, alkoxy, —OCF$_3$, —CN, alkyl, halogen, —NR$^5$R$^6$, —NR$^5$C(O)R$^7$, —C(O)NR$^5$R$^6$, —NR$^5$S(O$_2$)R$^7$, —S(O$_2$)NR$^5$R$^6$, —S(O$_2$)R$^7$, —C(O)R$^7$, —C(O)OR$^5$, —CF$_3$, -alkyleneNR$^5$R$^6$, -alkyleneNR$^6$C(O)R$^7$, -alkyleneNR$^6$S(O$_2$)R$^7$, alkenyl, —NR$^5$C(O)NR$^5$R$^6$, -alkyleneNR$^5$C(O)OR$^7$, CHO and —C=NOR$^5$;

$R^5$ is hydrogen or alkyl;

$R^6$ is hydrogen, alkyl, aryl, aralkyl, heteroaryl or heteroaralkyl;

$R^7$ is alkyl, aryl, aralkyl, heteroaryl or heteroaralkyl;

$R^8$ is alkyl, —OH or hydroxyalkyl;

$R^{11}$ is 1 to 4 moieties and each $R^{11}$ is independently selected from group the consisting of hydrogen, alkoxy, alkyl, halogen, —OH, —OCF$_3$, CN and —CF$_3$; and X is 1 to 4 moieties and each X is independently selected from hydrogen, alkyl, aryl, cycloalklyl, heteroaryl, heterocyclyl, halogen, $R^4$-substituted aryl, $R^4$-substituted cycloalklyl, $R^4$-substituted heteroaryl, $R^4$-substituted heterocyclyl, —CF$_3$, —OCF$_3$, —OR$^2$, —CN, —C(O)R$^2$, —S(O$_2$)R$^7$, —C(O)NR$^5$R$^6$, —C(O)OR$^7$ and —NR$^5$C(O)R$^7$.

This invention is also directed to pharmaceutical compositions for the treatment of metabolic disorders such as obesity, those disorders associated with obesity and eating disorders such as hyperphagia. In one aspect, this invention is directed to the method of treatment of metabolic disorders such as such as obesity, and eating disorders such as hyperphagia. Another embodiment includes a method of treating an eating disorder which comprises administering to a mammal in need of such treatment an amount of a first compound, said first compound being a compound of formula I; and a second compound, said second compound being an antiobesity and/or anorectic agent wherein the amounts of the first and second compounds result in the therapeutic desired effect. In another aspect, this invention is also directed to pharmaceutical compositions for the treatment of obesity which comprise an obesity treating amount of at least one compound of formula 1, or a pharmaceutically acceptable salt or solvate of said compound and a pharmaceutically acceptable carrier.

U.S. Provisional Patent Application Ser. No. 60/434,306, was filed on Dec. 18, 2002, the contents of said application are hereby incorporated by reference in their entirety.

DETAILED DESCRIPTION

The present invention relates to compounds that are represented by structural formula I, or a pharmaceutically acceptable salt or solvate thereof, wherein the various moieties are as described above.

These novel compounds can be potent MCH antagonists and also can be selective against other receptors, such as $M_2$ receptor, h-HT transporter.

The dashed line portion of formula I, as represented by

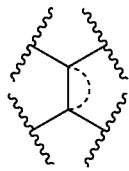

along with the accompanying single bond, together represent

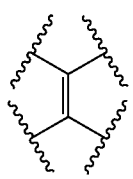

a double bond,

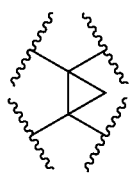

a cyclopropyl or

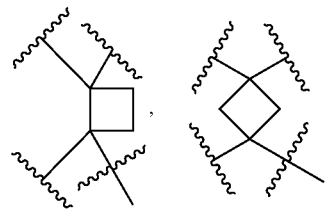

a cyclobutyl.

One aspect of the invention include those compounds of formula I wherein Ar is aryl, heteroaryl or $R^4$-substituted aryl.

Another aspect of the invention include those compounds of formula I wherein $R^1$ is hydrogen, alkyl, aryl, cycloalkylalkyl, cycloalkyl, heteroaryl, $R^4$-substituted heteroaryl, -alkylenyl-C(O)$R^8$, —C(O)NR$^2$R$^3$, —C(O)OR$^7$ or —S(O$_2$)R$^7$.

Another aspect of the invention include those compounds of formula I wherein $R^2$ and $R^3$ are ethyl or methyl or $R^2$ and $R^3$ are joined together and with the nitrogen to which they are attached, form a heterocyclyl ring of formula

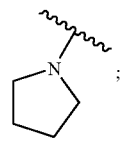

and $R^7$ is methyl or —CH(CH$_3$)$_2$.

Another aspect of the invention include those compounds of formula I wherein wherein $R^4$ is 1 or 2 moieties, each $R^4$ is independently selected from the group consisting of hydrogen, heterocyclylalkyl, —CN, halogen, —NR$^5$R$^6$, —CF$_3$, -alkyleneNR$^5$R$^6$,

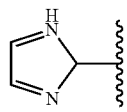

and CHO.

Another aspect of the invention include those compounds of formula I wherein

Ar is aryl, heteroaryl or $R^4$-substituted aryl;

$R^1$ is hydrogen, alkyl, aryl, cycloalkylalkyl, cycloalkyl, heteroaryl, $R^4$-substituted heteroaryl, -alkylenyl-C(O)$R^8$, —C(O)NR$^2$R$^3$, —C(O)OR$^7$ or —S(O$_2$)R$^7$;

$R^2$ and $R^3$ are alkyl or $R^2$ and $R^3$ are joined together and with the nitrogen to which they are attached, form a heterocyclyl ring;

$R^4$ is 1 or 2 moieties, each $R^4$ is independently selected from the group consisting of hydrogen, heterocyclylalkyl, —CN, halogen, —NR$^5$R$^6$, —CF$_3$, -alkyleneNR$^5$R$^6$,

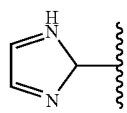

and CHO;

$R^5$ and $R^6$ are alkyl;

$R^7$ is methyl or —CH(CH$_3$)$_2$; and

X is 1 or 2 moieties and X is halogen or —CF$_3$.

Additional aspects of the invention include those compounds of formula I wherein Ar is heteroaryl or $R^4$-substituted aryl;

$R^1$ is hydrogen, alkyl, aryl, cycloalkylalkyl, cycloalkyl, heteroaryl, $R^4$-substituted heteroaryl, -alkylenyl-C(O)$R^8$, —C(O)N$R^2R^3$, —C(O)O$R^7$ or —S(O$_2$)$R^7$;

$R^2$ and $R^3$ are alkyl or $R^2$ and $R^3$ are joined together and with the nitrogen to which they are attached, form a heterocyclyl ring;

$R^4$ is 1 or 2 moieties, each $R^4$ is independently selected from the group consisting of hydrogen, heterocyclylalkyl, —CN, -alkyleneN$R^5R^5$,

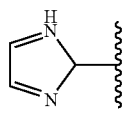

and CHO;

$R^5$ and $R^6$ are alkyl;

$R^7$ is methyl or —CH(CH$_3$)$_2$; and

X is 1 or 2 moieties and X is chloro, fluoro or —CF$_3$.

Alternative aspects of the invention also include those compounds wherein

Ar is

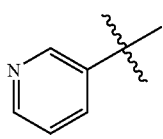

or $R^4$-substituted phenyl;

$R^1$ is hydrogen, methyl, benzyl, cyclopropylmethyl, cyclopropyl,

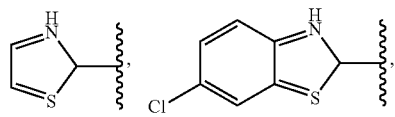

-alkylenyl-C(O)$R^8$, —C(O)N$R^2R^3$, —C(O)O$R^7$ or —S(O$_2$)$R^7$;

$R^2$ and $R^3$ are methyl or ethyl or $R^2$ and $R^3$ are joined together and with the nitrogen to which they are attached, form a heterocyclyl ring of formula

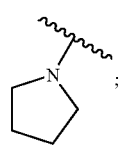

$R^4$ is 1 or 2 moieties, each $R^4$ is independently selected from the group consisting of hydrogen,

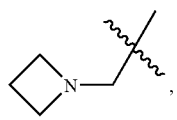

—CN, -methyleneN$R^5R^6$,

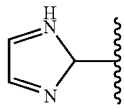

and CHO;

$R^5$ and $R^6$ are methyl;

$R^7$ is methyl or —CH(CH$_3$)$_2$;

$R^8$ is —OH; and

X is 2 moieties and X is chloro, fluoro or —CF$_3$.

Preferably Ar is

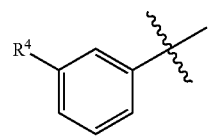

and $R^4$ is independently selected from the group consisting of hydrogen,

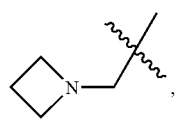

—CN, -methyleneN$R^5R^6$,

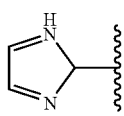

and CHO.

Additional aspects of the invention include those compounds of formula I wherein $R^{11}$ is hydrogen, alkoxy or —OH. Preferably, $R^{11}$ is methoxy.

Additional aspects of the invention include those compounds of formula I wherein X is substituted on the parent ring as follows

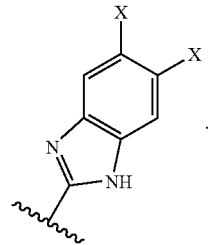

Preferably, X is fluoro, chloro or —CF$_3$.

Additional aspects of the invention include those compounds of formula I wherein dashed line portion of formula I, as represented by

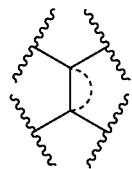

along with the accompanying single bond, together represent

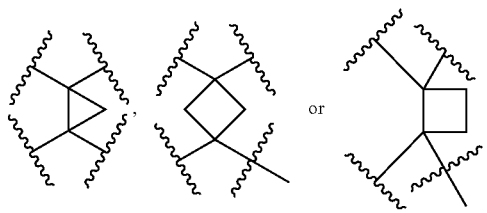

Additional aspects of the invention include those compounds of formula I wherein the dashed line of

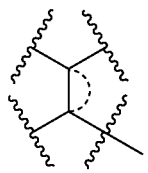

along with the adjoining single bond, together represent a double bond;

Ar is heteroaryl or $R^4$-substituted aryl;

$R^1$ is hydrogen, alkyl, aryl, cycloalkylalkyl, cycloalkyl, heteroaryl, $R^4$-substituted heteroaryl, -alkylenyl-C(O)$R^8$, —C(O)N$R^2R^3$, —C(O)O$R^7$ or —S(O$_2$)$R^7$;

$R^2$ and $R^3$ are alkyl or $R^2$ and $R^3$ are joined together and with the nitrogen to which they are attached, form a heterocyclyl ring;

$R^4$ is 1 or 2 moieties, each $R^4$ is independently selected from the group consisting of hydrogen, heterocyclylalkyl, —CN, halogen, —N$R^5R^6$, —CF$_3$, -alkyleneN$R^5R^6$,

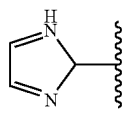

and CHO;

$R^5$ is hydrogen or alkyl;

$R^6$ is hydrogen, alkyl, aryl, aralkyl, heteroaryl or heteroaralkyl;

$R^7$ is alkyl, aryl, aralkyl, heteroaryl or heteroaralkyl;

$R^8$ is alkyl, —OH or hydroxyalkyl;

$R^{11}$ is hydrogen, alkoxy or —OH; and

X is 1 to 4 moieties and each X is independently selected from hydrogen, halogen and —CF$_3$.

Additional aspects of the invention include those compounds of formula I wherein the dashed line of

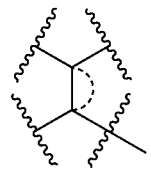

along with the adjoining single bond, together represent a cyclopropyl of formula

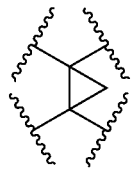

Ar is heteroaryl or $R^4$-substituted aryl;

$R^1$ is hydrogen, alkyl, aryl, cycloalkylalkyl, cycloalkyl, heteroaryl, $R^4$-substituted heteroaryl, -alkylenyl-C(O)R , —C(O)N$R^2R^3$, —C(O)O$R^7$ or —S(O$_2$)$R^7$;

$R^2$ and $R^3$ are alkyl or $R^2$ and $R^3$ are joined together and with the nitrogen to which they are attached, form a heterocyclyl ring;

$R^4$ is 1 or 2 moieties, each $R^4$ is independently selected from the group consisting of hydrogen, heterocyclylalkyl, —CN, halogen, —N$R^5R^6$, —CF$_3$, -alkyleneN$R^5R^6$,

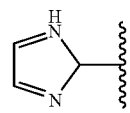

and CHO;

$R^5$ is hydrogen or alkyl;

$R^6$ is hydrogen, alkyl, aryl, aralkyl, heteroaryl or heteroaralkyl;

$R^7$ is alkyl, aryl, aralkyl, heteroaryl or heteroaralkyl;

$R^8$ is alkyl, —OH or hydroxyalkyl;

$R^{11}$ is hydrogen, alkoxy or —OH; and

X is 1 to 4 moieties and each X is independently selected from hydrogen, halogen and —CF$_3$.

Still additional preferred embodiments of formula I include compounds selected from the group consisting of Examples 1a, 1b, 1c, 1d, 1e, 1f, 1g, 1h, 1j, 1k, 1l, 1m, 1n, 1o, 1p, 1q, 1r, 1s, 1t, 1u, 1v, 1w, 1x, 1y, 1z, 1aa, 1ab, 23a, 23b, 23c, 24a, 24b, 25a, 25b, 25c, 26a, 26b, 27a, 27b, 27c, 28a, 29a, 29b and 29c.

Other embodiments of the claimed invention include those methods of treatment with the compounds of formula I wherein the eating disorder is hyperphagia and wherein the metabolic disorder is obesity.

Another embodiment is a method of treating a disorder associated with obesity comprising administering to a mammal in need of such treatment a therapeutically effective amount of at least one compound of formula I, or a pharmaceutically acceptable salt or solvate of said compound. Specific examples of disorders associated with obesity include but are not limited to type II diabetes, insulin resistance, hyperlipidemia or hypertension.

Another embodiment includes a method of treating an eating disorder which comprises administering to a mammal in need of such treatment an amount of a first compound, said first compound being a compound of formula I or a pharmaceutically acceptable salt or solvate of said compound; and a second compound, said second compound being an antiobesity and/or anorectic agent selected from the group consisting of a $\beta_3$ agonist, a thryomimetic agent, an anorectic agent and an NPY antagonist;

wherein the amounts of the first and second compounds result in the therapeutic desired effect.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", "cycloalkyl" and so forth.

As used above, and throughout the specification, the following terms, unless otherwise indicated, shall be understood to have the following meanings:

"Alkyl" means an aliphatic hydrocarbon group, which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. Non-limiting examples of suitable alkyl groups include methyl, ethyl, n-propyl, isopropyl, n-butyl, and t-butyl.

"Alkenyl" means an aliphatic hydrocarbon group comprising at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. The term "substituted alkenyl" means that the alkenyl group may be substituted by one or more substituents which may be the same or different, each substituent being independently selected from the group consisting of halogen, alkyl, aryl, cycloalkyl, cyano, and alkoxy. Non-limiting examples of suitable alkenyl groups include ethenyl, propenyl, n-butenyl, and 3-methylbut-2-enyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Alkylene" means an alkanediyl group commonly having free valencies on two carbon atoms. Non-limiting examples include methylene, ethylene, propylene and the like.

"Aryl" means an aromatic monocyclic or multicyclic ring system comprising about 6 to about 14 carbon atoms, preferably about 6 to about 10 carbon atoms. Included in the definition of aryl are fused aryls such as indenyl, napthalenyl, anthracenyl and indolinyl. Fused aryls can be attached to the parent moiety either through the saturated or unsaturated portions of the ring. The aryl group can be unsubstituted or substituted on the ring with one or more substituents which may be the same or different, each being independently selected from $R^4$ or $R^8$. Non-limiting examples of suitable aryl groups include phenyl and naphthyl. The "aryl" group can also be substituted by linking two adjacent carbons on its aromatic ring via a combination of one or more carbon atoms and one or more oxygen atoms such as, for example, methylenedioxy, ethylenedioxy, and the like.

"Aralkyl" means an aryl-alkyl-group in which the aryl and alkyl are as previously described. Preferred aralkyls comprise a lower alkyl group. Non-limiting examples of suitable aralkyl groups include benzyl, 2-phenethyl and a naphthlenylmethyl. The bond to the parent moiety is through the alkyl. The term "substituted aralkyl" means that the aralkyl group may be substituted by one or more substituents which may be the same or different, each substituent being independently selected from $R^4$.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted on the ring by replacing an available hydrogen on the ring by one or more substituents which may be the same or different, each being independently $R^4$, $R^8$ or two moieties on adjacent carbons of the cycloalkyl ring can be joined together to form a methylenedioxy or ethylenedioxy group. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkylalkyl group in which the cycloalkyl and alkyl groups are as previously described. The cycloalkyl portion of cycloalkylalkyl can be optionally substituted on the ring by replacing an available hydrogen on the ring by one or more substituents which may be the same or different, each being independently $R^4$ or $R^8$. The bond to the parent moiety is through the alkyl group.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted on the ring by replacing an available hydrogen on the ring by one or more substituents which may be the same or different, each being independently selected from $R^4$ or $R^8$. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridyl-methyl, 2-(furan-3-yl)ethyl and quinolin-3-ylmethyl. The bond to the parent moiety is through the alkyl. The "heteroaralkyl" can be optionally substituted on the ring by replacing an available hydrogen on the ring by one or more substituents which may be the same or different, each being independently selected from $R^4$ or $R^8$.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted on the ring by replacing an available hydrogen on the ring or hydrogen(s) on any nitrogen(s) suitably by one or more substituents which may be the same or different, each being independently selected from $R^4$ or $R^8$. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, thiophenyl, tetrahydrothiophenyl, morpholinyl and the like.

"Heterocyclylalkyl" means heterocyclyl-alkyl-group in which the heterocyclyl and alkyl are as previously described. The heterocyclyl ring can be optionally substituted on the ring by replacing an available hydrogen on the ring or hydrogen(s) on any nitrogen(s) suitably by one or more substituents which may be the same or different, each being independently selected from $R^8$. The nitrogen or sulfur atom of the heterocyclyl can be optionally oxidized to the corresponding N-oxide, S-oxide or S,S-dioxide. Non-limiting examples of suitable heterocyclylalkyl groups include

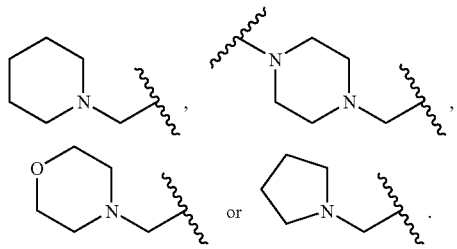

The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Mammal" means humans and other mammalian animals.

"Patient" includes both human and other animals.

It should also be noted that any heteroatom with unsatisfied valences in the text, schemes, examples, structural formulae, and Tables herein is assumed to have the hydrogen atom or atoms to satisfy the valences.

The terms "at least one" compound or "one or more compounds" means one to three compounds, preferably one compound.

When any variable (e.g., aryl, heterocycle, $R^2$, etc.) occurs more than once in any substituent or in Formula I, its definition at each occurrence is independent of its definition at every other occurrence. Also, combinations of substituents and/or variables are permissible only if such combinations result in stable compounds.

The compounds of Formula I can be administered as racemic mixtures or enantiomerically pure compounds within the scope of the present invention.

As used herein, the term "composition" is intended to encompass a product comprising the specified ingredients in the specified amounts, as well as any product which results, directly or indirectly, from combination of the specified ingredients in the specified amounts.

The compounds of formula I can form salts, solvates and prodrugs, which are also within the scope of this invention. Reference to a compound of formula I herein is understood to include reference to salts, solvates and prodrugs thereof, unless otherwise indicated.

Solvates of the compounds of the invention are also contemplated as within the scope of the present invention. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Prodrugs of the compounds of the invention are also contemplated within the scope of this invention. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compound of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" and the like, is intended to equally apply to the salt and solvate of enantiomers, stereoisomers, rotamers, tautomers or racemates of the inventive compounds.

Compounds of Formula I can be highly selective, high affinity Melanin Concentrating Hormone (MCH) receptor antagonists useful for the treatment of obesity.

An aspect of this invention is a method of treating a mammal (e.g., human) having a disease or condition mediated by MCH by administering a therapeutically effective amount of at least one compound of Formula I, or a pharmaceutically acceptable salt or solvate of said compound to the mammal.

"Effective amount" or "therapeutically effective amount" is meant to describe an amount of compound of the present invention effective to treat a mammal (e.g., human) having a disease or condition mediated by MCH, and thus producing the desired therapeutic effect.

A preferred dosage is about 0.001 to 100 mg/kg of body weight/day of the compound of Formula I. An especially preferred dosage is about 0.01 to 30 mg/kg of body weight/day of a compound of Formula I, or a pharmaceutically acceptable salt or solvate of said compound.

Still yet another aspect of this invention is a method of treating obesity comprising administering to a mammal in need of such treatment a therapeutically effective amount of at least one compound of Formula I, or a pharmaceutically acceptable salt or solvate of said compound.

A further aspect of this invention is a method for treating eating and metabolic disorders such as bulimia and anorexia comprising administering to a mammal a therapeutically effective amount of at least one compound of Formula I, or a pharmaceutically acceptable salt or solvate of said compound.

Another aspect of this invention is a method for treating hyperlipidemia comprising administering to a mammal a therapeutically effective amount of at least one compound of Formula I or a pharmaceutically acceptable salt or solvate of said compound.

Another aspect of this invention is a method for treating cellulite and fat accumulation comprising administering to a mammal a therapeutically effective amount of at least one compound of Formula I, or a pharmaceutically acceptable salt or solvate of said compound.

Another aspect of this invention is directed to a method for treating type II diabetes comprising administering to a mammal a therapeutically effective amount of at least one compound of Formula I or a pharmaceutically acceptable salt or solvate of said compound.

In addition to the "direct" effect of the compounds of this invention on the MCH subtype, there are diseases and conditions that can benefit from the weight loss such as, for example, insulin resistance, impaired glucose tolerance, Type II Diabetes, hypertension, hyperlipidemia, cardiovascular disease, gall stones, certain cancers, and sleep apnea.

This invention is also directed to pharmaceutical compositions, which comprise at least one compound of Formula I, or a pharmaceutically acceptable salt or solvate of said compound and at least one pharmaceutically acceptable carrier.

This invention is also directed to pharmaceutical compositions for the treatment of obesity which comprise an obesity treating amount of at least one compound of Formula I, or a pharmaceutically acceptable salt or solvate of said compound and at least one pharmaceutically acceptable carrier.

Still yet other aspects of this invention are combinations of a compound of Formula I, or a pharmaceutically acceptable salt or solvate of said compound and other compounds as described below.

Accordingly, included within the invention is a method for treating obesity comprising administering to a mammal (e.g., a female or male human)

a. an amount of a first compound, said first compound being a compound of Formula I, or a pharmaceutically acceptable salt or solvate of said compound; and b. an amount of a second compound, said second compound being an antiobesity and/or anorectic agent such as a $\beta_3$ agonist, a thyromimetic agent, an anoretic agent, or an NPY antagonist and/or optionally a pharmaceutically carrier, vehicle or diluent, wherein the amounts of the first and second compounds result in a therapeutic effect (treating obesity).

Another aspect of this invention is a kit comprising:

a. an amount of a compound of Formula I, or a pharmaceutically acceptable salt or solvate of said compound and a pharmaceutically acceptable carrier, vehicle or diluent in a first unit dosage form;

b. an amount of an antiobesity and/or anorectic agent such as a $\beta_3$ agonist, a thyromimetic agent, an anoretic agent, or an NPY antagonist and a pharmaceutically acceptable carrier, vehicle or diluent in a second unit dosage form; and c. means for containing said first and second dosage forms wherein the amounts of the first and second compounds result in a therapeutic effect.

Preferred antiobesity and/or anorectic agents (taken singly or in any combination thereof) in the above combination methods, combination compositions and combination kits are:

phenylpropanolamine, ephedrine, pseudoephedrine, phentermine, a cholecystokinin-A (hereinafter referred to as CCK-A) agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (hereinafter referred to as "leptin"), a leptin analog, a leptin receptor agonist, a galanin antagonist or a GI lipase inhibitor or decreaser (such as orlistat). Other useful anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

Another aspect of this invention is a method of treating diabetes comprising administering to a mammal (e.g., a female or male human)

a. an amount of a first compound, said first compound being a compound of Formula I, or a pharmaceutically acceptable salt or solvate of said compound; and b. an amount of a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone or GW-1929, a sulfonylurea, glipazide, glyburide, or chlorpropamide wherein the amounts of the first and second compounds result in a therapeutic effect.

This invention is also directed to a pharmaceutical combination composition comprising: a therapeutically effective amount of a composition comprising a first compound, said first compound being a compound of Formula I, or a pharmaceutically acceptable salt or solvate of said compound;

a second compound, said second compound being an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide; and optionally a pharmaceutical carrier, vehicle or diluent.

Another aspect of this invention is a kit comprising:

a. an amount of a compound of Formula I, or a pharmaceutically acceptable salt or solvate of said compound and a pharmaceutically acceptable carrier, vehicle or diluent in a first unit dosage form;

b. an amount of an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a PPAR-gamma ligand such as troglitazone, rosaglitazone, pioglitazone, or GW-1929, a sulfonylurea, glipazide, glyburide, or chlorpropamide and a pharmaceutically acceptable carrier, vehicle or diluent in a second unit dosage form; and c. means for containing said first and second dosage forms wherein the amounts of the first and second compounds result in a therapeutic effect.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

Compounds of Formula I can be produced by processes known to those skilled in the art using either solution phase or solid phase synthesis as shown in the following reaction schemes, in the preparations and examples below.

Synthesis

The invention disclosed herein is exemplified by the following preparations and examples which should not be construed to limit the scope of the invention which is defined in the appended claims. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The observed parent ion using electro spray ionization are given.

The following abbreviations are utilized throughout the experimental procedures described below:

SEMCI means 2-(trimethylsilyl)ethoxymethyl chloride;
DIBAL means disobutyl aluminum hydride;
EtONa means sodium ethoxide;
EtOH means ethanol;
MeOH means methanol;
Bn means benzyl;
Me means methyl;
H$_3$CN means acetonitrile;
TFA means trifluoroacetic acid;
THF means tetrahydrofuran;
DCM means dichloromethane;
DMF means N,N-dimethylformamide;
Boc means Butoxycarbonyl;
NMR means nuclear magnetic resonance spectroscopy;
MS means mass spectrometry;
room temperature or rt (ambient) means about 25° C.;
NaBH(OAc$_3$) means sodium triacetoxyborohydride;

Alternative mechanistic pathways and analogous structures within the scope of the invention would be apparent to those skilled in the art.

EXPERIMENTAL EXAMPLES

The following examples illustrate the preparation of some of the compounds of the invention and are not to be construed as limiting the scope of the invention disclosed herein.

All stereoisomers and tautomeric forms of these compounds are contemplated. Compounds such as 1a, 1b can be prepared from (1-Benzyl-piperidin-4-ylidene)-(4-bromophenyl)-acetonitrile (see Scheme 1).

Scheme 1

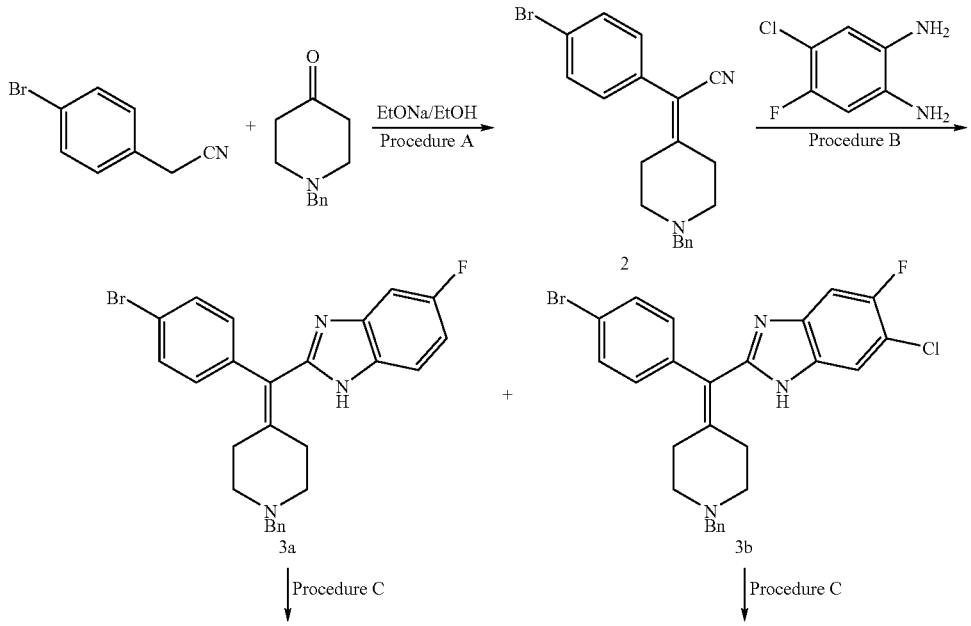

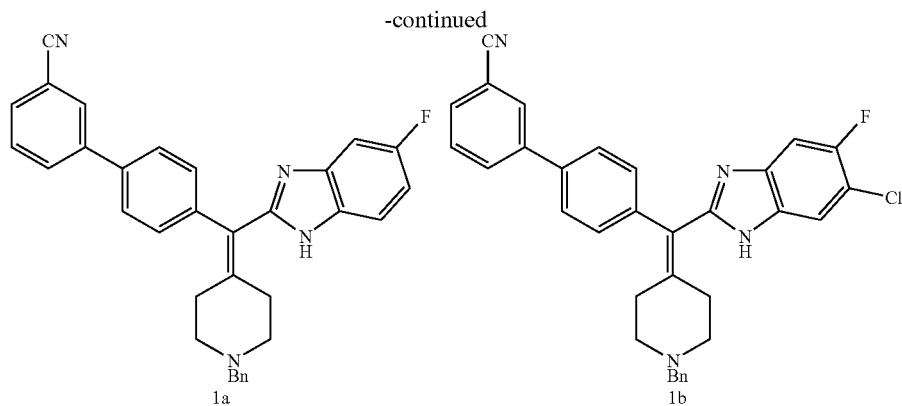
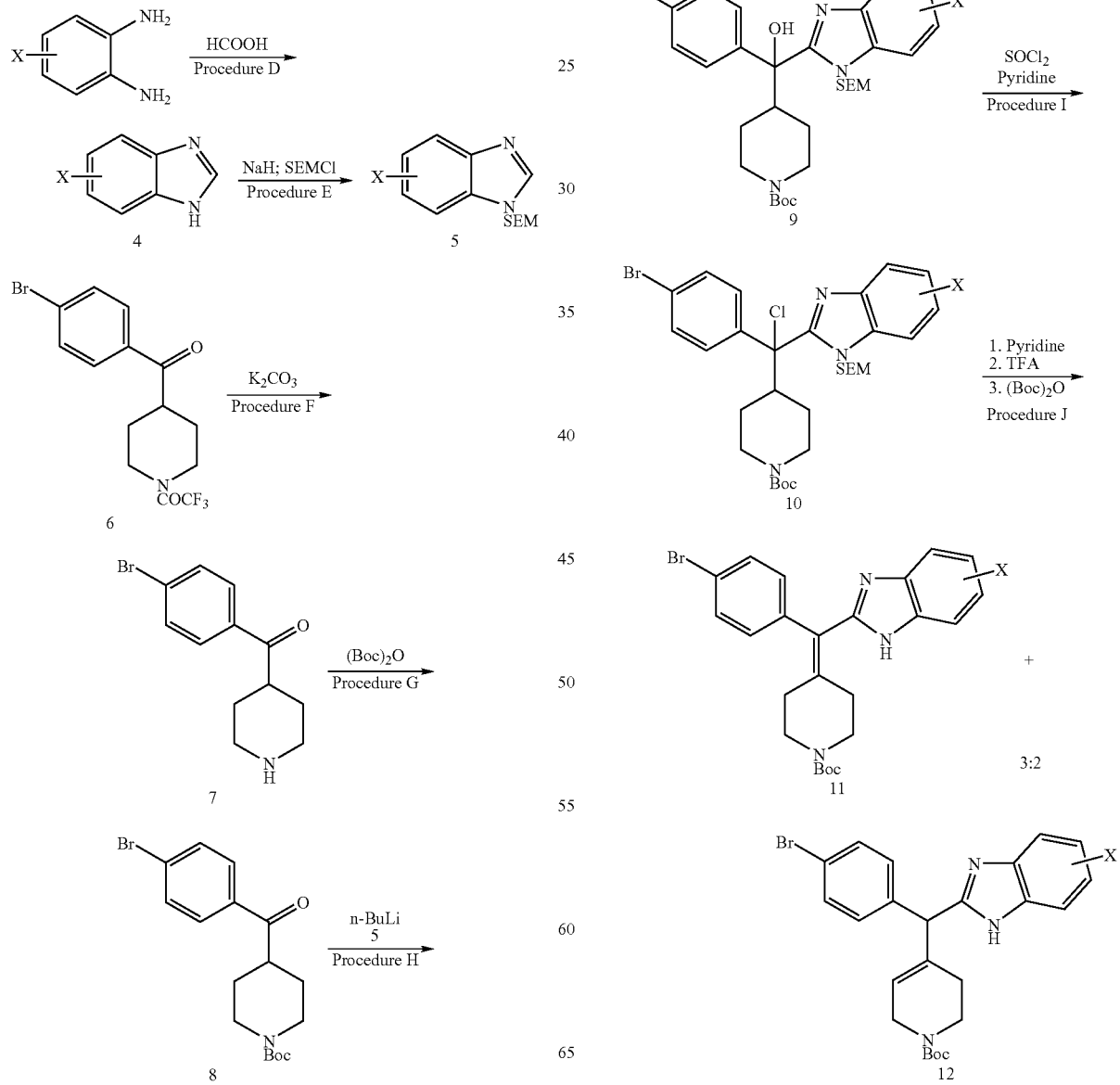

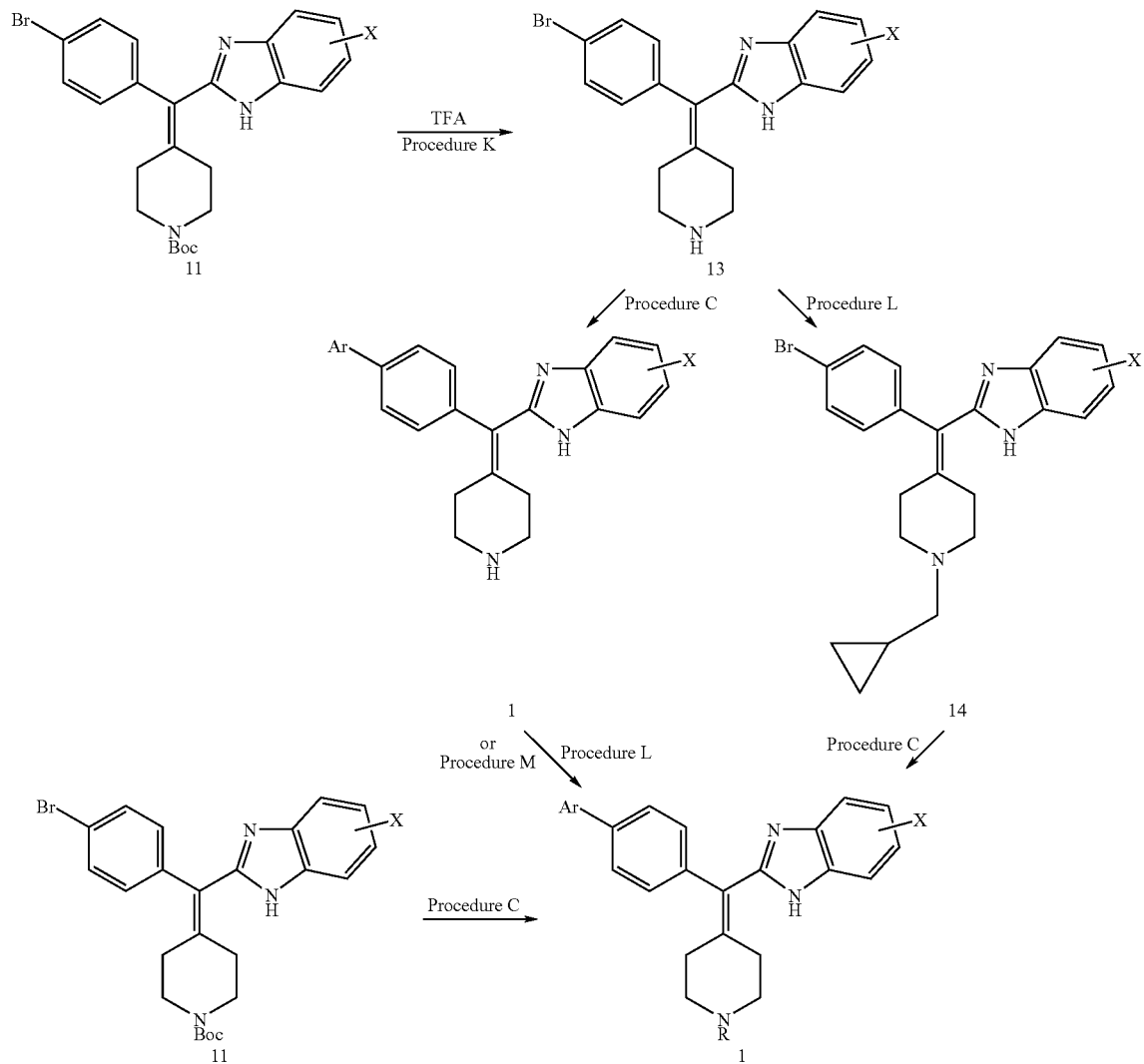
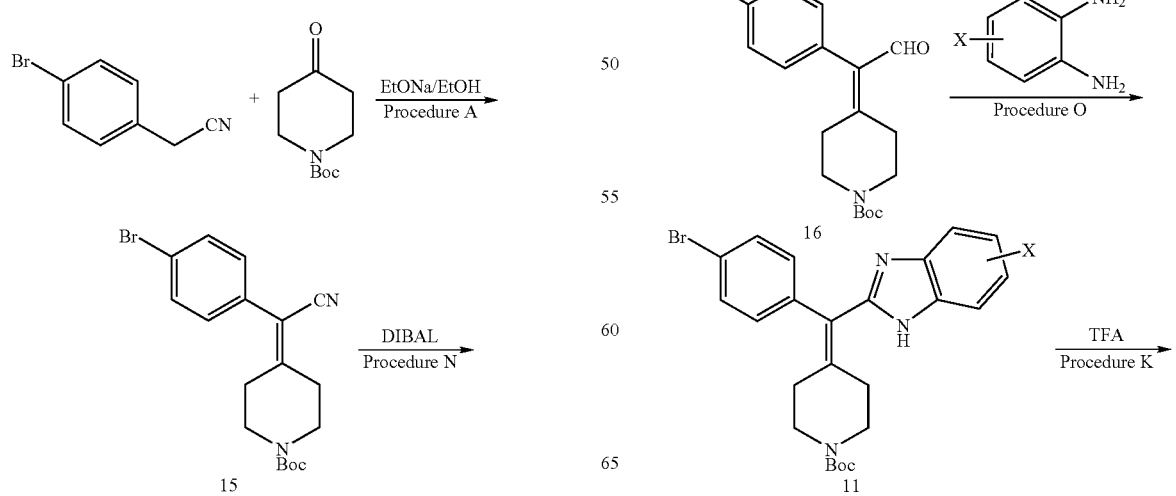

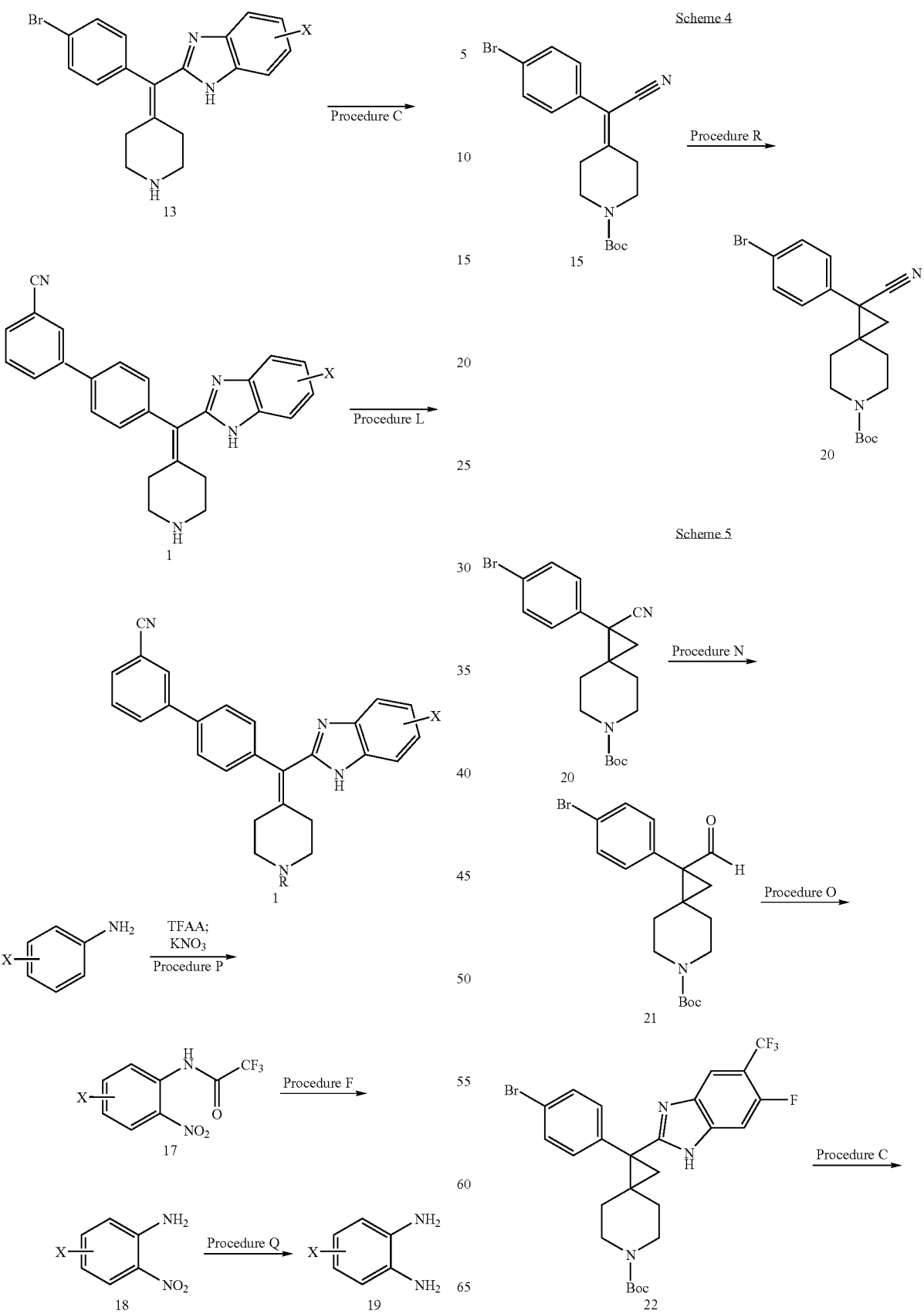

-continued

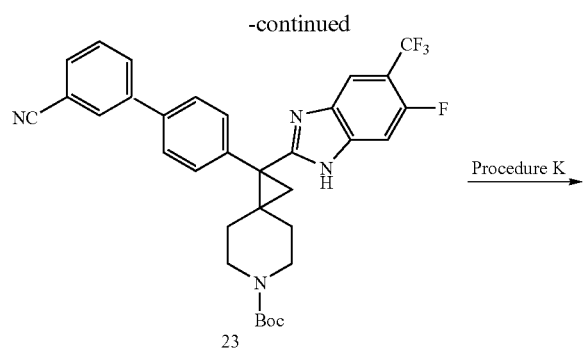

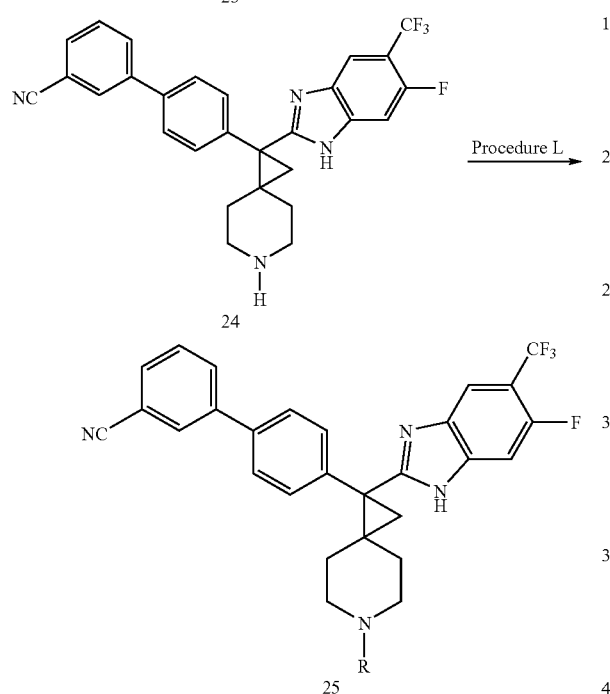

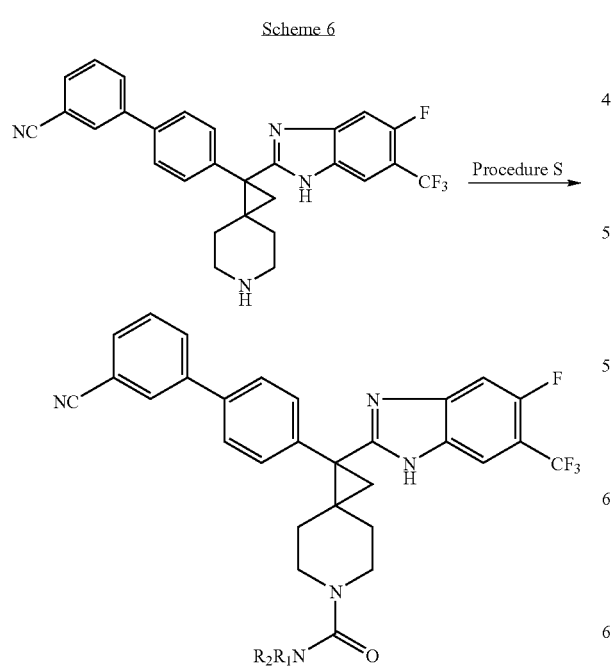

Scheme 7

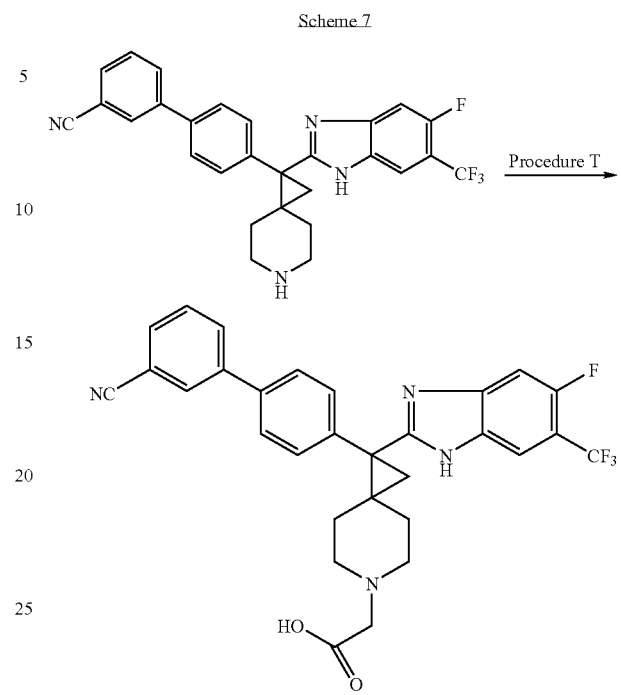

Scheme 7

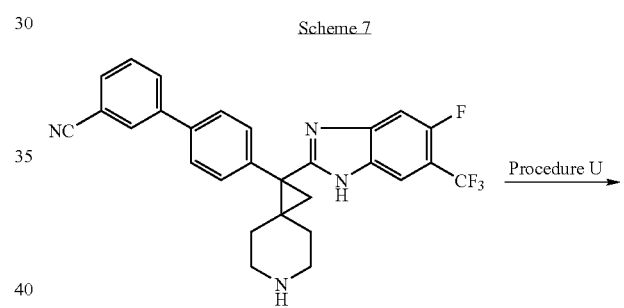

Experimental Procedures

Procedure A:

To a stirred solution of 5.0 g (25.5 mmol) of 4-bromophenylacetonitrile in 150 mL of ethanol was added 2.0 g (28 mmol) of sodium ethoxide at room temperature. After 10 min., 4.8 g (24 mmol) of t-butyl-4-oxo-piperidinecarboxylate was added, and the mixture was stirred at the same temperature for 3 days. It was quenched with 200 mL of saturated aqueous NH$_4$Cl and concentrated to a volume of ca. 250 mL. The aqueous solution was extracted with three 200 mL portions of ether. The combined organic extracts were washed with 100 mL of brine and concentrated. The residue was chromatographed eluting with a gradient of from 5–30% ethyl acetate in hexanes to give 7.9 g of compound 15. Calcd m/z for $C_{18}H_{21}BrN_2O_2H^+$=377; found m/z=377.

Compound 2 can be prepared analogously. Calcd m/z for $C_{20}H_{19}BrN_2.H^+$=369; found m/z=369.

Procedure B:

A mixture of 0.37 g (1 mmol) of compound 2 and 0.16 g (1 mmol) of 4-chloro,5-fluoro-o-phenylenediamine in 4 mL of polyphosphoric acid was stirred at 200° C. for 4 h and poured into 60 mL of dilute $NH_4OH$. It was extracted with three 60 mL portions of ethyl acetate. The combined organic extracts were washed with 60 mL of brine and concentrated. The residue was chromatographed eluting with a gradient of from 2 to 10% methanol (MeOH) in dichloromethane (DCM) plus 1% $NH_4OH$ to give 0.06 g of compound 3a and 0.14 g of compound 3b. 3a: Calcd m/z for $C_{26}H_{23}BrFN_3$.$H^+$=478; found m/z=478. 3b: Calcd m/z for $C_{26}H_{22}BrClFN_3.H^+$=512; found m/z=512.

Procedure C:

A mixture of 0.45 g (1 mmol) of compound 13c, 0.18 g (1.1 mmol) of 3-cyanophenylboronic acid, 0.11 g (0.1 mmol) of $Pd(PPh_3)_4$ in 0.6 mL of 2N aqueous $Na_2CO_3$ and 6 mL of methanol-toluene (1:1) in a sealed tube was heated under reflux for 6 h. It was diluted with 60 mL of methanol, and filtered. The filtrate was concentrated and the residue was purified by silica gel chromatography eluting with gradient from 3–10% methanol in dichloromethane containing 1% $NH_4OH$ to give 0.43 g of compound 1r as a pale yellow solid. Calcd m/z for $C_{27}H_{20}F_4N_4.H^+$=477; found m/z=477.

Alternatively, this reaction could be performed using microwave conditions as follows:

A mixture of 0.055 g (0.1 mmol) of compound 3b, 0.02 g (0.13 mmol) of 3-cyanophenylboronic acid, 0.1 g (0.01 mmol) of $Pd(PPh_3)_4$ in 0.3 mL of 2N aqueous $Na_2CO_3$ and 4 mL of methanol-toluene (1:1) in a sealed tube was heated at 120° C. for 10 min under microwave irradiation in a SmithCreator apparatus (Personal Chemistry, Inc.) using temperature control. It was diluted with 30 mL of methanol, and filtered. The filtrate was concentrated and the residue was purified by preparative TLC eluting with 7% methanol in dichloromethane containing 1% $NH_4OH$ to give 0.044 g of compound 1b. Calcd m/z for $C_{33}H_{26}ClFN_4.H^+$=533; found m/z=533.

The following compounds can be prepared analogously.

| Compound | Structure | Formula (M + 1) | MS Calcd | (MH+) Found |
|---|---|---|---|---|
| 1a | 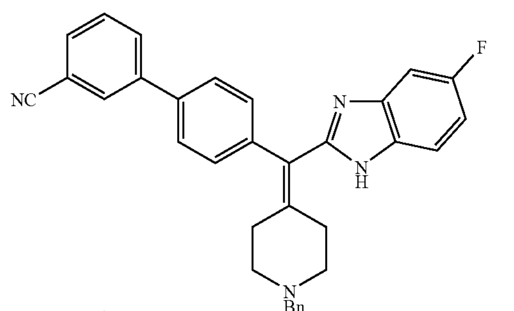 | $C_{33}H_{27}FN_4.H^+$ | 499 | 499 |
| 1b | 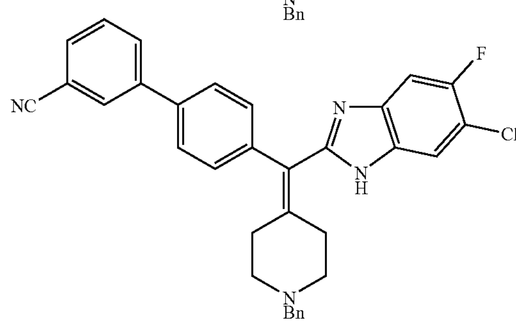 | $C_{33}H_{26}ClFN_4.H^+$ | 533 | 533 |
| 1c | 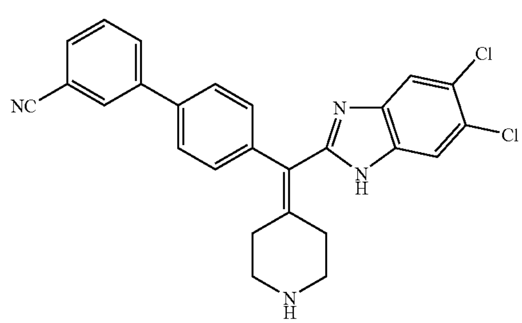 | $C_{26}H_{20}Cl_2N_4.H^+$ | 459 | 459 |

-continued
| Compound | Structure | Formula (M + 1) | MS Calcd | (MH+) Found |
|---|---|---|---|---|
| 1d | 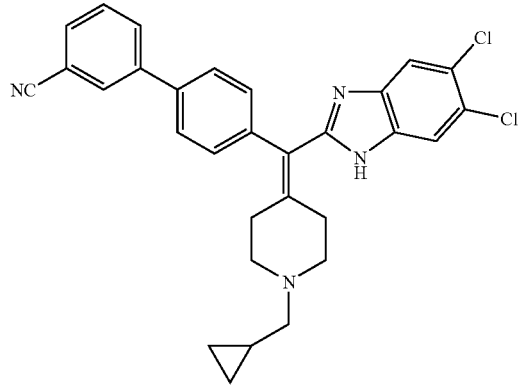 | $C_{30}H_{26}Cl_2N_4 \cdot H^+$ | 513 | 513 |
| 1h | 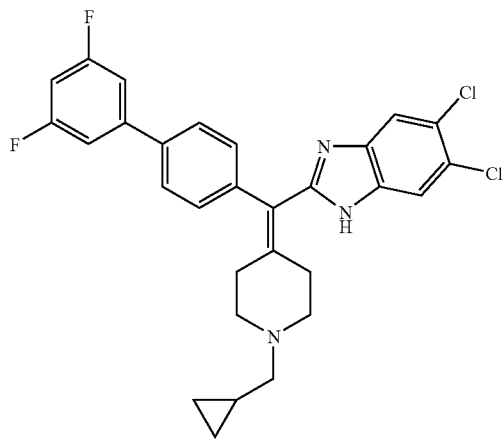 | $C_{29}H_{25}Cl_2F_2N_3 \cdot H^+$ | 524 | 524 |
| 1i | 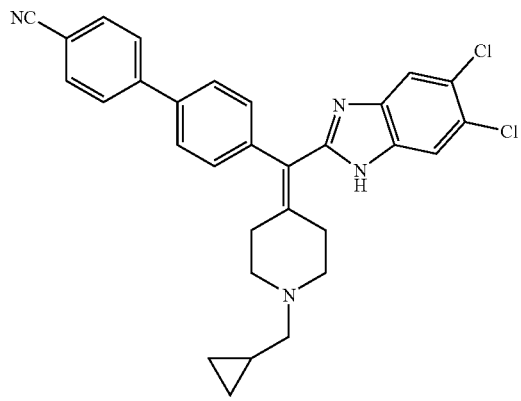 | $C_{30}H_{26}Cl_2N_4 \cdot H^+$ | 513 | 513 |

-continued

| Compound | Structure | Formula (M + 1) | MS Calcd | (MH+) Found |
|---|---|---|---|---|
| 1j | 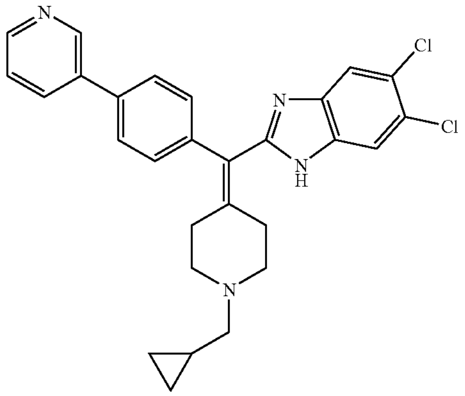 | $C_{28}H_{26}Cl_2N_4 \cdot H^+$ | 489 | 489 |
| 1k | 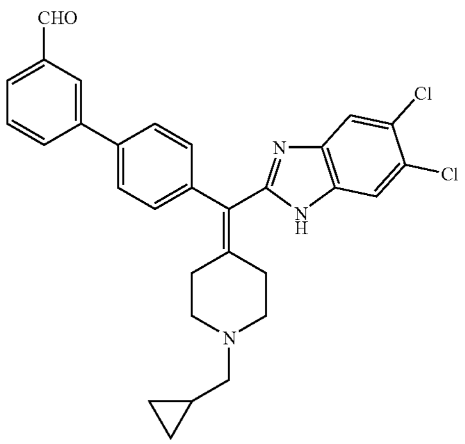 | $C_{30}H_{27}Cl_2N_3O \cdot H^+$ | 516 | 516 |
| 1n | 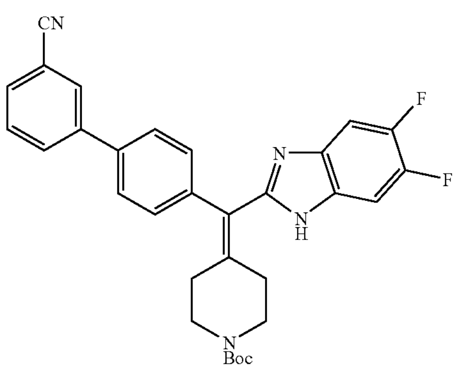 | $C_{31}H_{28}F_2N_4O_2 \cdot H^+$ | 527 | 527 |
| 1r | 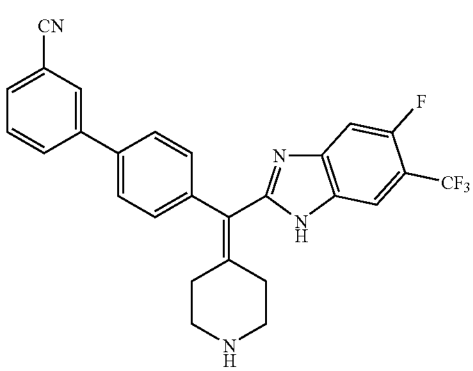 | $C_{27}H_{20}F_4N_4 \cdot H^+$ | 477 | 477 |

-continued

| Compound | Structure | Formula (M + 1) | MS Calcd | (MH+) Found |
|---|---|---|---|---|
| 1t | 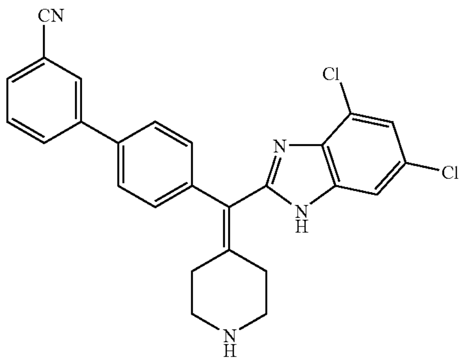 | $C_{26}H_{20}Cl_2N_4 \cdot H^+$ | 459 | 459 |
| 23a | 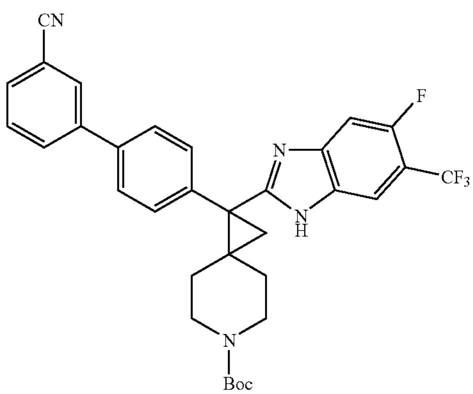 | $C_{33}H_{29}F_4N_4O_2^+$ | 590 | 590 |
| 23b | 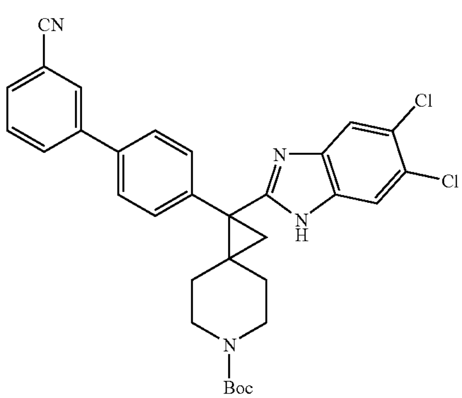 | $C_{32}H_{29}Cl_2N_4O_2 \cdot H^+$ | 573 | 573 |

-continued

| Compound | Structure | Formula (M + 1) | MS Calcd | (MH+) Found |
|---|---|---|---|---|
| 23c | (structure: 3-cyanophenyl-phenyl-cyclopropane-spiro-piperidine(N-benzyl)-benzimidazole with 5,6-dichloro) | $C_{34}H_{28}Cl_2N_4 \cdot H^+$ | 563 | 563 |

Procedure D:

To a suspension of 5.3 g (30 mmol) of 4,5-dichloro-o-phenylenediamine in 10 mL of H$_2$O were added 5 mL of HCOOH and 10 mL of concentrated HCl. The solution was stirred under reflux for 2 h and quenched with 150 mL of dilute NAOH. It was extracted with three portions of 250 mL of ethyl acetate. The combined organic extracts were washed with 80 mL of brine and concentrated to give 5.4 g of compound 4a.

The following compounds can be prepared analogously.

| Compound | Structure | Formula (M + 1) | MS Calcd | (MH+) Found |
|---|---|---|---|---|
| 4a | 5,6-dichlorobenzimidazole | $C_7H_4Cl_2N_4 \cdot H^+$ | 187 | 187 |
| 4b | 5,6-difluorobenzimidazole | $C_7H_4F_2N_4 \cdot H^+$ | 155 | 155 |

Procedure E:

To a stirred solution of 2.8 g (15 mmol) of compound 4a in 25 mL of DMF was added 0.75 g (60%, 18.8 mmol) of NaH. After 30 min, a solution of 3.15 g (18.8 mmol) of Me$_3$SiCH$_2$CH$_2$OCH$_2$Cl in 5 mL of DMF was added. The mixture was stirred at room temperature for 2 h, and quenched with 150 mL of H$_2$O. It was extracted with three 120 mL portions of ether. The combined organic extracts were washed with 60 mL of brine and concentrated. The residue was chromatographed on silica gel eluting with a gradient from 20 to 90% ethyl acetate in hexanes to give 2.95 g of compound 5a.

The following compounds can be prepared analogously.

| Compound | Structure | Formula (M + 1) | MS Calcd | (MH+) Found |
|---|---|---|---|---|
| 5a | 5,6-dichloro-1-SEM-benzimidazole | $C_{13}H_{18}Cl_2N_2OSi \cdot H^+$ | 317 | 317 |

-continued

| Compound | Structure | Formula (M + 1) | MS Calcd | (MH+) Found |
|---|---|---|---|---|
| 5b | F-benzimidazole-F with SEM | $C_{13}H_{18}F_2N_2OSi.H^+$ | 285 | 285 |

Procedure F:

To a solution of 12 g (33 mmol) of compound 6 (Anandan Palani, et al, *J. Med. Chem.* 2002, 45, 3143) in 100 mL of methanol-H$_2$O (1:3) was added 10 g (72 mmol) of K$_2$CO$_3$. The solution was stirred at room temperature for 18 h and concentrated to a volume of ca. 70 mL. It was diluted with 100 mL of H$_2$O and extracted with three 150 mL portions of dichloromethane. The combined organic extracts were washed with 50 mL of brine and concentrated. The residue was chromatographed on silica gel eluting with a gradient from 3 to 12% methanol in dichloromethane containing 1% NH$_4$OH to give 7 g of compound 7. Calcd m/z for $C_{12}H_{14}BrNO.H^+$=268; found m/z=268.

Procedure H:

To a stirred solution of 1 g (3.15 mmol) of compound 5a in 10 mL of THF was added 1.3 mL (3.25 mmol) of n-BuLi at −78° C. After 20 min, a solution of 0.92 g (2.5 mmol) of compound 8 was added and the mixture was warmed to 0° C. over 1 h. It was quenched with 50 mL of H$_2$O and extracted with three 70 mL portions of dichloromethane. The combined organic extracts were washed with 30 mL of brine, and concentrated. The residue was purified by silica gel chromatography eluting with a gradient from 1 to 3% methanol in dichloromethane containing 1% NH$_4$OH to give 1.7 g of compound 9a.

The following compounds can be prepared analogously.

| Compound | Structure | Formula (M + 1) | MS Calcd | (MH+) Found |
|---|---|---|---|---|
| 9a | Br-phenyl-C(OH)(piperidine-Boc)-benzimidazole(SEM)-diCl | $C_{30}H_{40}BrCl_2N_3O_4Si.H^+$ | 686 | 686 |
| 9b | Br-phenyl-C(OH)(piperidine-Boc)-benzimidazole(SEM)-diF | $C_{30}H_{40}BrF_2N_3O_4Si.H^+$ | 654 | 654 |

Procedure G:

To a solution of 7 g (26 mmol) of compound 7 in 150 mL of methanol was added 6.5 g (30 mmol) of (Boc)$_2$O. The mixture was stirred at room temperature for 2 h and concentrated. The residue was recrystalized from methanol to give compound 8. Calcd m/z for $C_{17}H_{22}BrNO_3.H^+$=368; found m/z=368.

Procedure I:

To a stirred solution of 3.5 g (5 mmol) of compound 9a in 20 mL of pyridine was added 0.5 mL (7 mmol) of SOCl$_2$ at room temperature. After 1 h it was concentrated and the residue was chromatographed over silica gel eluting with 10% ethyl acetate in hexanes to give 3.1 g of compound 10a.

The following compounds can be prepared analogously.

| Compound | Structure | Formula (M + 1) | MS Calcd | (MH+) Found |
|---|---|---|---|---|
| 10a | 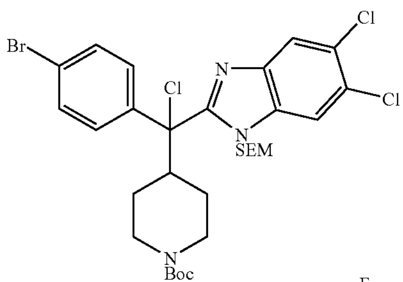 | $C_{30}H_{39}BrCl_3N_3O_3Si.H^+$ | 704 | 704 |
| 10b | 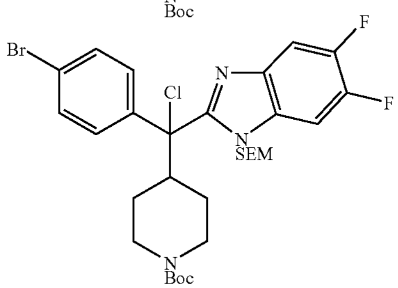 | $C_{30}H_{39}BrClF_2N_3O_3Si.H^+$ | 672 | 672 |

Procedure J

A solution of 2.8 g (4 mmol) of compound 10a in 5 mL of pyridine in a sealed tube was heated at 150° C. under microwave irradiation for 35 min. The solvent was evaporated and the residue was treated with 20 mL of trifluoroacetic acid-dichloromethane (1:1) at room temperature for 18 h. It was concentrated and the residue was dissolved in 50 mL of methanol. To this solution were added 0.5 g of $K_2CO_3$ and 1 g (4.6 mmol) of $(Boc)_2O$. The mixture was stirred at room temperature for 2 h and concentrated. The residue was diluted with 60 mL of $H_2O$, extracted with three 80 mL portions of ether. The combined organic extracts were washed with 50 mL of brine, and concentrated. The residue was purified by silica gel chromatography eluting with a gradient from 10 to 25% ethyl acetate in hexanes to give 0.92 g of compound 11a and 0.51 g of compound 12a.

The following compounds can be prepared analogously.

| Compound | Structure | Formula (M + 1) | MS Calcd | (MH+) Found |
|---|---|---|---|---|
| 11a | 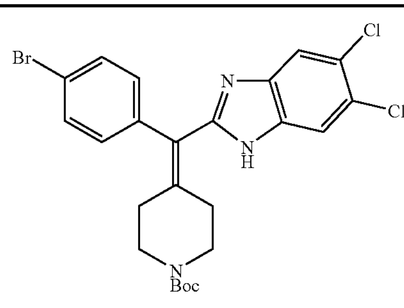 | $C_{24}H_{24}BrCl_2N_3O_2.H^+$ | 538 | 538 |
| 12a | 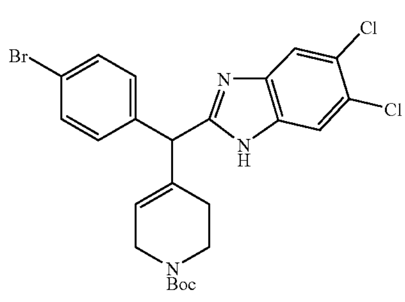 | $C_{24}H_{24}BrCl_2N_3O_2.H^+$ | 538 | 538 |

-continued

| Compound | Structure | Formula (M + 1) | MS Calcd | (MH+) Found |
|---|---|---|---|---|
| 11b | 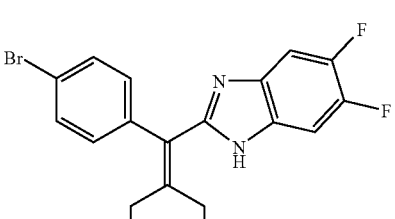 | $C_{24}H_{24}BrF_2N_3O_2 \cdot H^+$ | 504 | 504 |
| 12b | 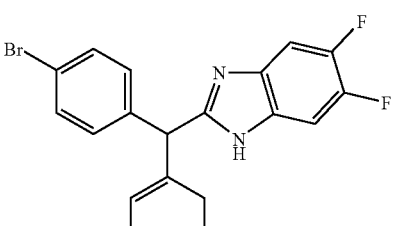 | $C_{24}H_{24}BrF_2N_3O_2 \cdot H^+$ | 504 | 504 |

Procedure K

To a stirred solution of 0.26 g (0.47 mmol) of compound 11c in 2 mL of dichloromethane was added 2 mL of trifluoroacetic acid at room temperature. After 18 h, it was concentrated and the residue was chromatographed over silica gel eluting with a gradient of 1–8% methanol in dichloromethane containing 1% NH$_4$OH to give 0.195 g of 13c as a yellow foam. Calcd m/z for $C_{20}H_{16}BrF_4N_3 \cdot H^+$= 454; found m/z=454.

The following compounds can be prepared analogously.

| Compound | Structure | Formula (M + 1) | MS Calcd | (MH+) Found |
|---|---|---|---|---|
| 13a | 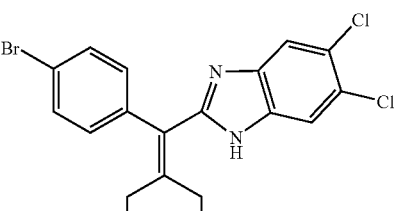 | $C_{19}H_{16}BrCl_2N_3 \cdot H^+$ | 438 | 438 |
| 13c | 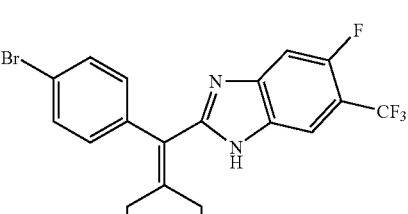 | $C_{20}H_{16}BrF_4N_3 \cdot H^+$ | 454 | 454 |

-continued

| Compound | Structure | Formula (M + 1) | MS Calcd | (MH+) Found |
|---|---|---|---|---|
| 13d | 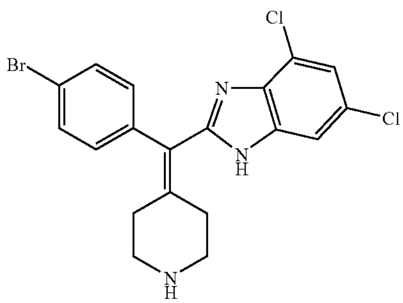 | $C_{19}H_{16}BrCl_2N_3 \cdot H^+$ | 438 | 438 |
| 1o | 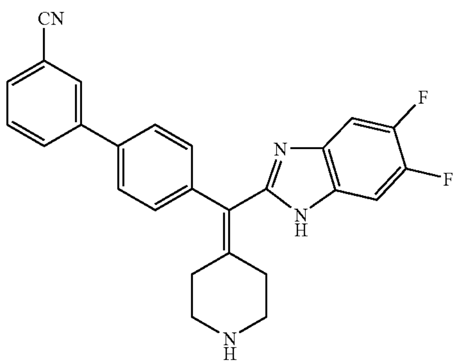 | $C_{26}H_{20}F_2N_4 \cdot H^+$ | 427 | 427 |
| 24a | 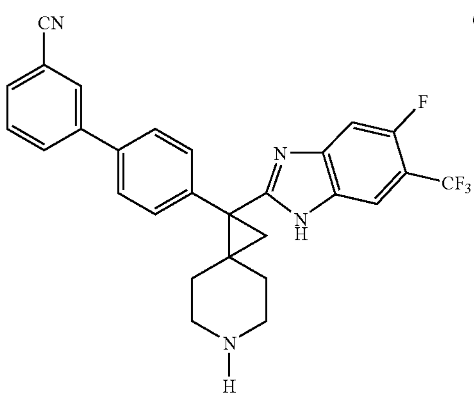 | $C_{28}H_{23}F_4N_4 \cdot H^+$ | 491 | 491 |
| 24b | 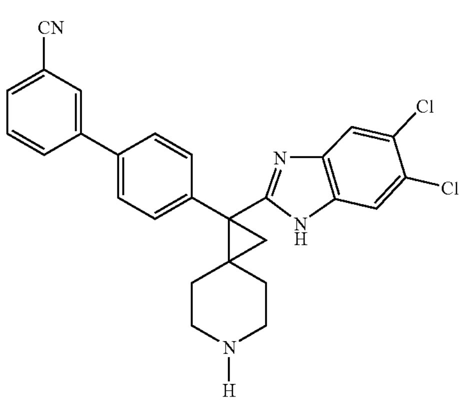 | $C_{27}H_{21}Cl_2N_4 \cdot H^+$ | 473 | 473 |

| Compound | Structure | Formula (M + 1) | MS Calcd | (MH+) Found |
|---|---|---|---|---|
| 1ab | (structure: 3-cyanophenyl-biphenyl with methoxy, benzimidazole bearing F and CF3, piperidine NH) | $C_{28}H_{22}F_4N_4O \cdot H^+$ | 507 | 507 |

Procedure L

To a stirred solution of 0.072 g (0.15 mmol) of compound 1r in 3 mL of dichloromethane was added 0.014 g (0.2 mmol) of cyclopropanecarboxaldehyde and 0.065 g (0.3 mmol) of NaBH(OAc)$_3$ at room temperature. After 18 h the mixture was concentrated and the residue was chromatographed over silica gel eluting with a gradient from 2–8% of methanol in dichloromethane to give 0.055 g of compound is as an oil. Calcd m/z for $C_{31}H_{26}F_4N_4{}^+$=530; found m/z=530 (M$^+$).

The following compounds were prepared analogously.

| Compound | Structure | Formula (M + 1) | MS Calcd | (MH+) Found |
|---|---|---|---|---|
| 14a | (structure: 4-bromophenyl, 5,6-dichlorobenzimidazole, piperidine N-CH2-cyclopropyl) | $C_{23}H_{22}BrCl_2N_3 \cdot H^+$ | 492 | 492 |
| 1d | (structure: 3-cyano-biphenyl, 5,6-dichlorobenzimidazole, piperidine N-CH2-cyclopropyl) | $C_{30}H_{26}Cl_2N_4 \cdot H^+$ | 513 | 513 |

-continued

| Compound | Structure | Formula (M + 1) | MS Calcd | (MH+) Found |
|---|---|---|---|---|
| 1e | 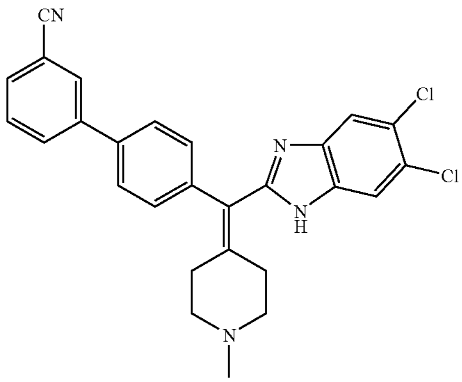 | $C_{27}H_{22}Cl_2N_4 \cdot H^+$ | 473 | 473 |
| 1f | 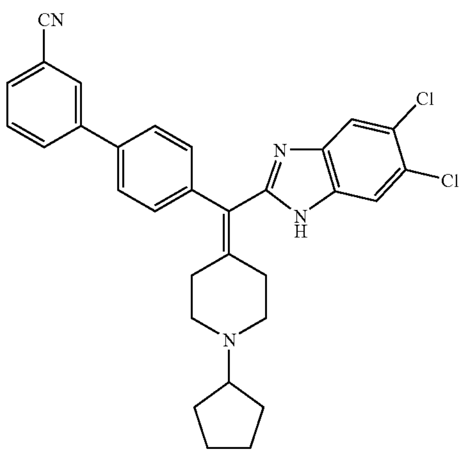 | $C_{31}H_{28}Cl_2N_4 \cdot H^+$ | 527 | 527 |
| 1l | 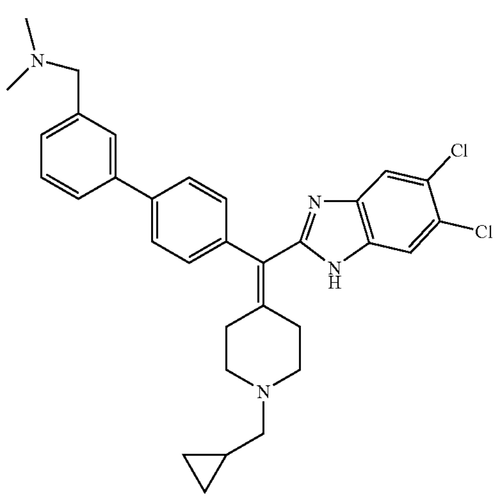 | $C_{32}H_{34}Cl_2N_4 \cdot H^+$ | 545 | 545 |

-continued

| Compound | Structure | Formula (M + 1) | MS Calcd | (MH+) Found |
|---|---|---|---|---|
| 1m | 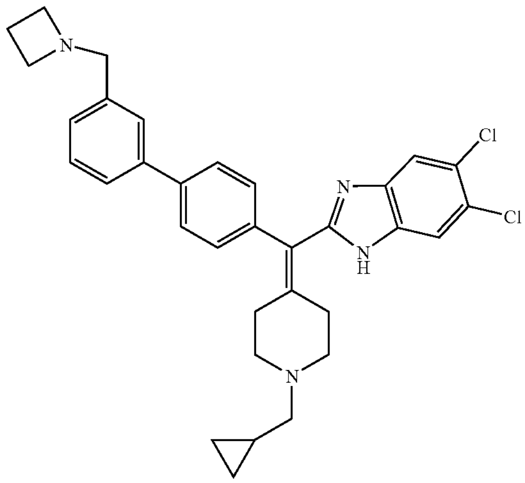 | $C_{33}H_{34}Cl_2N_4 \cdot H^+$ | 557 | 557 |
| 1p | 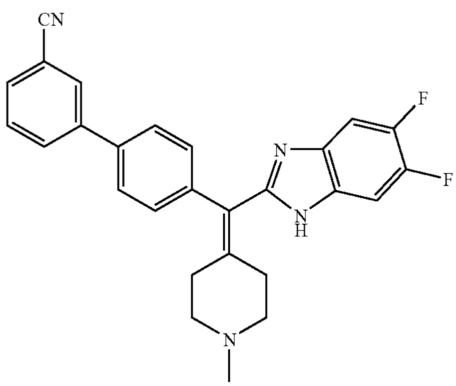 | $C_{27}H_{22}F_2N_4 \cdot H^+$ | 441 | 441 |
| 1q | 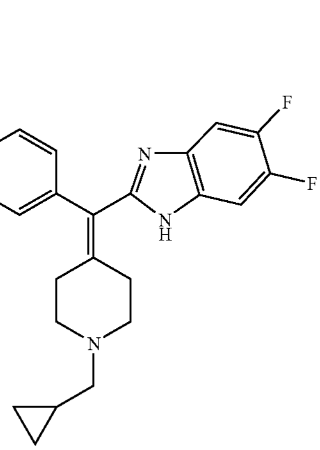 | $C_{30}H_{26}F_2N_4 \cdot H^+$ | 481 | 481 |

-continued

| Compound | Structure | Formula (M + 1) | MS Calcd | (MH+) Found |
|---|---|---|---|---|
| 1s | 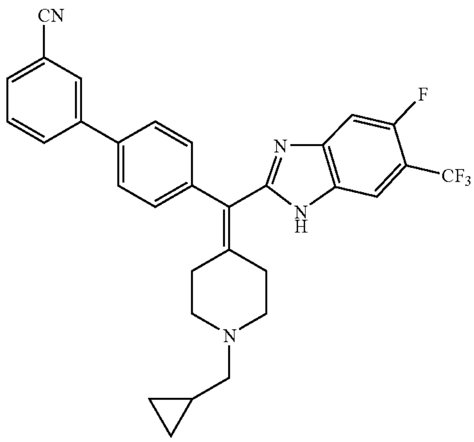 | $C_{31}H_{26}F_4N_4^+$ | 530 (M+) | 530 (M+) |
| 1u | 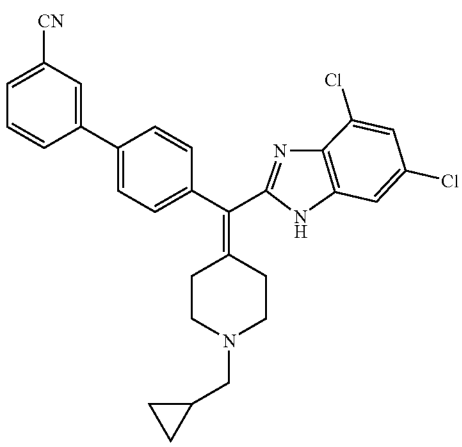 | $C_{30}H_{26}Cl_2N_4 \cdot H^+$ | 513 | 513 |
| 25a | 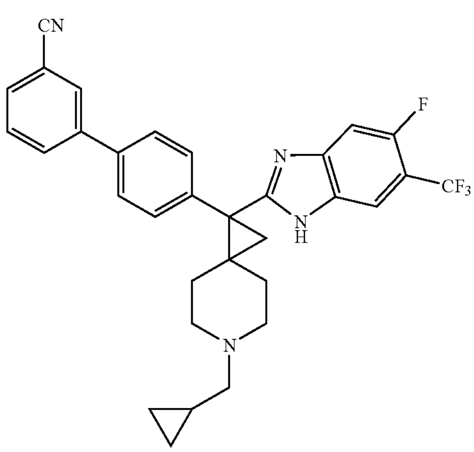 | $C_{32}H_{29}F_4N_4 \cdot H^+$ | 545 | 545 |

-continued
| Compound | Structure | Formula (M + 1) | MS Calcd (MH+) | Found |
|---|---|---|---|---|
| 25b | 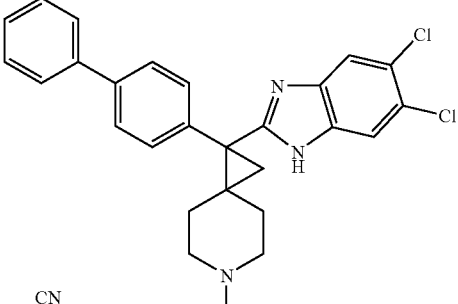 | $C_{31}H_{27}Cl_2N_4.H^+$ | 527 | 527 |
| 25c | 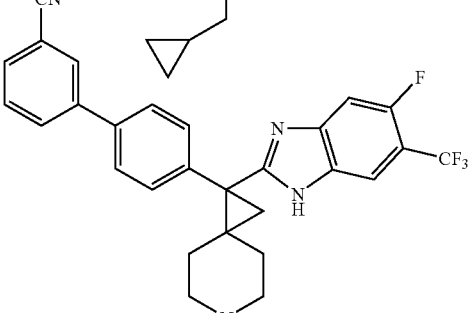 | $C_{35}H_{28}F_4N_4.H^+$ | 581 | 581 |
| 1aa | 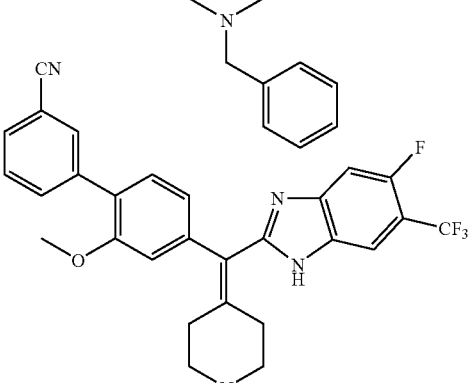 | $C_{32}H_{28}F_4N_4O.H^+$ | 561 | 561 |
Procedure M
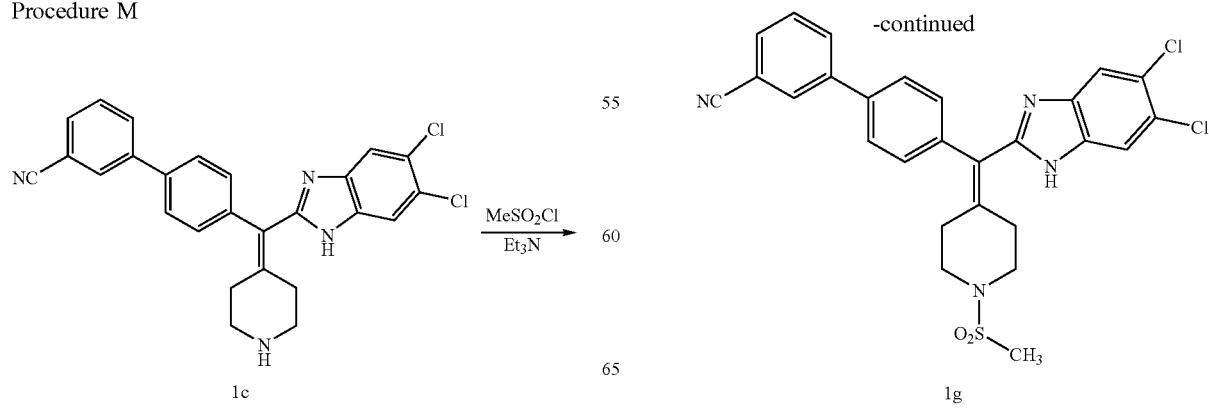

To a solution of 0.055 g (0.12 mmol) of compound 1c in 2 mL of dichloromethane were added 0.03 g (0.3 mmol) of Et$_3$N and 0.018 g (0.15 mmol) of MeSO$_2$Cl. The mixture was stirred at room temperature for 18 h and purified by preparative TLC eluting with 7% methanol in dichloromethane containing 1% NH$_4$OH to give 0.04 g of compound 1g. Calcd m/z for C$_{27}$H$_{22}$Cl$_2$N$_4$O$_2$S.H$^+$=537; found m/z=537.

The following compound was prepared analogously.

| Compound | Structure | Formula (M + 1) | MS Calcd | (MH+) Found |
|---|---|---|---|---|
| 1v | 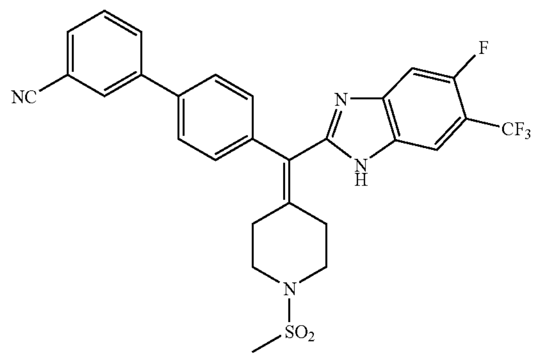 | C$_{28}$H$_{22}$F$_4$N$_4$O$_2$S.H$^+$ | 555 | 555 |
| 1w | 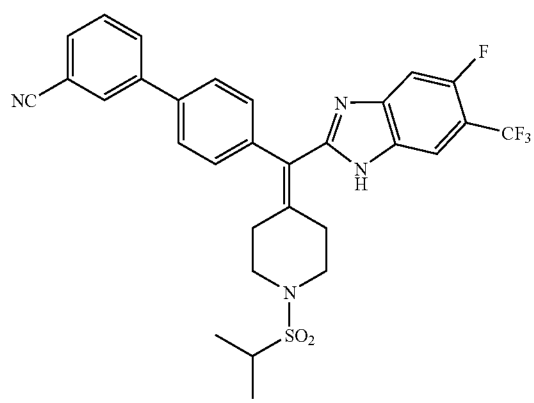 | C$_{30}$H$_{26}$F$_4$N$_4$O$_2$S.H$^+$ | 583 | 583 |
| 26a | 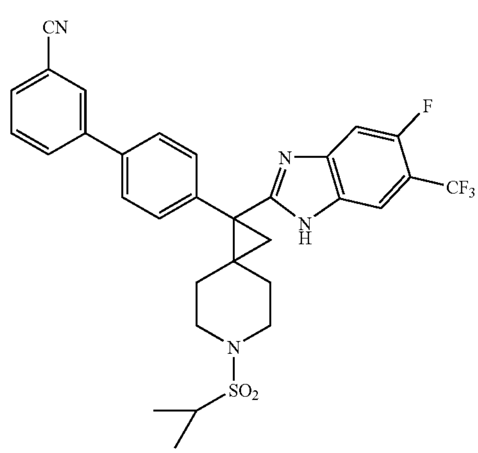 | C$_{31}$H$_{27}$F$_4$N$_4$O$_2$S.H$^+$ | 597 | 597 |

| Compound | Structure | Formula (M + 1) | MS Calcd | (MH+) Found |
|---|---|---|---|---|
| 26b | 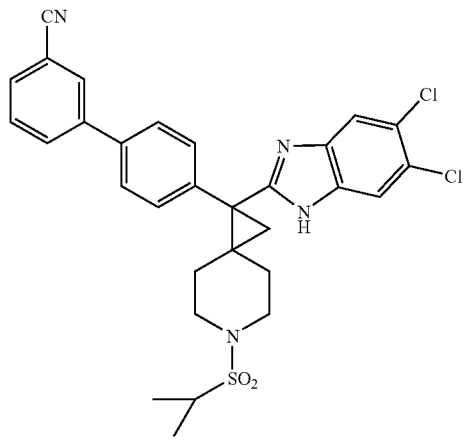 | $C_{30}H_{27}Cl_2N_4O_2S.H^+$ | 579 | 579 |

Procedure N

To a solution of 3.8 g (10 mmol) of compound 15 in 40 mL of dichloromethane was added 20 mL (20 mmol) of DIBAL in toluene at −78° C. The mixture was stirred at the same temperature for 3 h and quenched with 2 mL of methanol and 150 mL of 5% aqueous HCl. It was extracted with three 100 mL portions of dichloromethane. The combined organic extracts were washed with 80 mL of brine and concentrated. The residue was purified by silica gel chromatography eluting with 10 to 40% ethyl acetate in hexanes to give 0.95 g of compound 16. Calcd m/z for $C_{18}H_{22}BrNO_3.H^+$=380; found m/z=380.

The following compound was prepared analogously.

Procedure O

To a mixture of 2.8 g (7.4 mmol) of compound 16 in 10 mL of $NaHSO_3$ and 25 mL of ethanol was added 1.43 g (7.4 mmol) of compound 19a. The mixture was stirred under reflux for 40 h and concentrated. The residue was diluted with 60 mL of $H_2O$ and extracted with three 80 mL portions of ethyl acetate. The combined organic extracts were washed with 50 mL of brine and concentrated. The residue was purified by silica gel chromatography eluting with a gradient from 10 to 40% ethyl acetate in hexanes to give 1.1 g of compound 11c. Calcd m/z for $C_{25}H_{24}BrF_4N_3O_2.H^+$=556; found m/z=556.

| Compound | Structure | Analytical data |
|---|---|---|
| 21 | 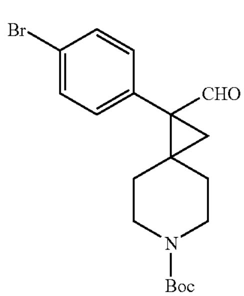 | $^1H$ NMR (400 MHz) δ 0.75–0.71(m, 1H) 1.44–1.50 (m, 10H) 1.47(d, 1H, J = 5.1 Hz) 1.71–1.76 (m, 2H) 1.89 (d, 1H, J = 5.1 Hz) 2.90–2.96 (m, 1H) 3.08–3.13 (m, 1H) 3.73–3.83 (m, 2H) 7.16 (d, 2H, J = 8 Hz, ArH) 7.52 (d, 2H, J = 8 Hz, ArH) 9.66 (s, 1H, CHO) |

The following compounds were prepared analogously.

| Compound | Structure | Formula (M + 1) | MS Calcd | (MH+) Found |
|---|---|---|---|---|
| 11c | 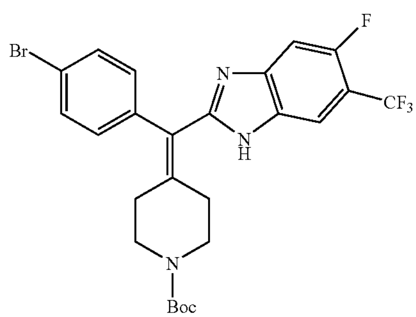 | $C_{25}H_{24}BrF_4N_3O_2 \cdot H^+$ | 556 | 556 |
| 11d | 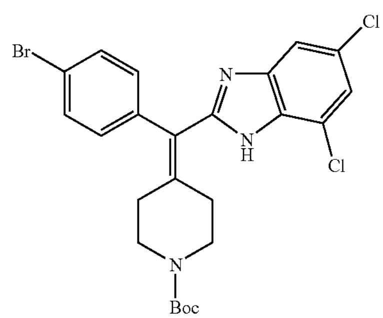 | $C_{24}H_{24}BrCl_2N_3O_2 \cdot H^+$ | 538 | 538 |
| 22 | 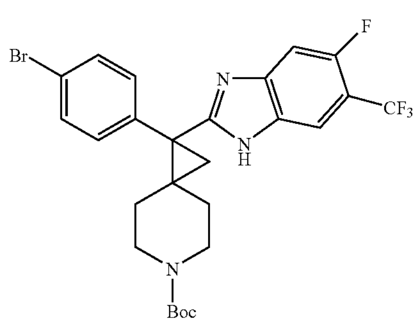 | $C_{26}H_{27}BrF_4N_3O_2 \cdot H^+$ | 568 | 568 |
| 11e | 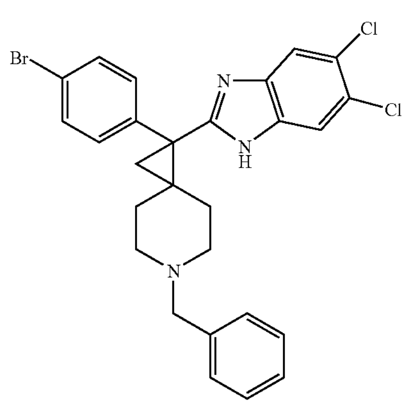 | $C_{27}H_{24}BrCl_2N_3 \cdot H^+$ | 542<br>540 | 542<br>540 |

Procedure P:

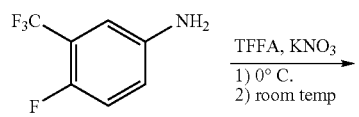

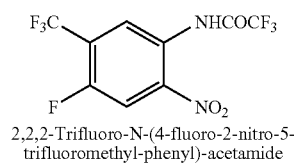

2,2,2-Trifluoro-N-(4-fluoro-2-nitro-5-trifluoromethyl-phenyl)-acetamide 2,2,2-Trifluoro-N-(4-fluoro-2-nitro-5-trifluoromethyl-phenyl)-acetamide To a stirred solution of 100 mL of trifluoroacetic anhydride was added 13.9 g (77.6 mmol) of 5-amino-2-fluorobenzotrifluoride slowly at 0° C. After 30 minutes, 8.63 g (85.4 mmol) of potassium nitrate was added in portions. The mixture was stirred at 0° C. for 1 hour and warmed to room temperature overnight. The reaction was poured into 800 mL of ice water; the solid was collected by vacuum filtration and dried under vacuum to give 18.8 g of compound 17a as a yellow powder. $^1$H NMR ($\delta$, CDCl$_3$) 11.2 (s, 1H, NH) 9.13 (d, 1H, J=6.4 Hz, ArH) 8.19 (d, 1H, J=9.4 Hz, ArH).

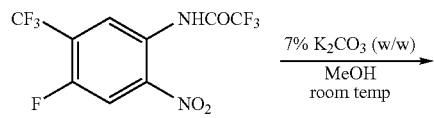

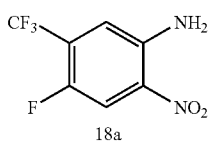

The trifluoroacetamide was hydrolyzed analogously to procedure F to give nitroaniline 18a as a yellow solid: Calcd for C$_7$H$_4$F$_4$N$_2$O$_2$.H$^+$=225; Found m/z=225.

Procedure Q

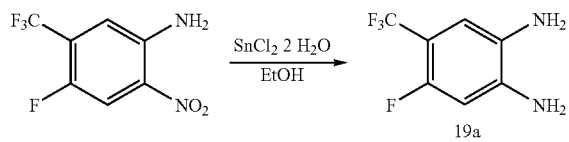

To a stirred solution of 11.35 g (50.6 mmol) of the nitroaniline 18a in 250 mL of ethanol was added 57.1 g (253 mmol) of tin (II) chloride dihydrate at room temperature. The reaction was heated at 65–70° C. for 45 minutes. The reaction was cooled and poured into 900 mL of ice water. It was basified to pH 8 with solid sodium bicarbonate and extracted with ethyl acetate. The combined organic extracts were washed with brine, dried over anhydrous sodium sulfate, and evaporated to give 9.33 g of compound 19a as a dark red solid. Calcd for C$_7$H$_6$F$_4$N$_4$.H$^+$=195; Found m/z=195.

Compound 19b was prepared analogously as a dark red solid: $^1$H NMR ($\delta$, CDCl$_3$) 6.81 (s, 1H, ArH) 6.60 (s, 1H, ArH) 3.68 (s, 2H, NH$_2$) 3.53 (s, 2H, NH$_2$).

Procedure R

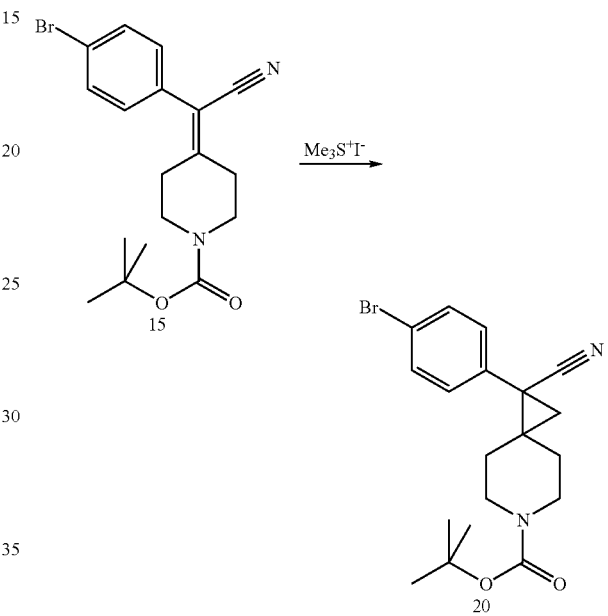

To a flask containing 3.61 g of potassium t-butoxide were added 60 mL of DMSO and 7.01 g of trimethylsulfonium iodide. The solution was stirred at room temperature for 1.5 hours and then a solution of 48 mL of DMSO containing 10.01 g of 4-[(4-Bromo-phenyl)-cyano-methylene]-piperidine-1-carboxylic acid tert-butyl ester was added. Stirring continued at room temperature overnight. The reaction was quenched with water and then brine. It was extracted with ethyl acetate, washed with water and brine, dried over MgSO4 and concentrated to an orange oil (9.96 g). m/z calculated for C$_{19}$H$_{24}$BrN$_2$O$_2$$^+$=391, found m/z=391 (M+H)$^+$ Procedure S:

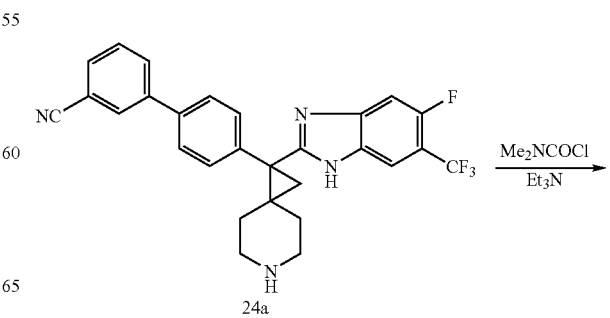

-continued

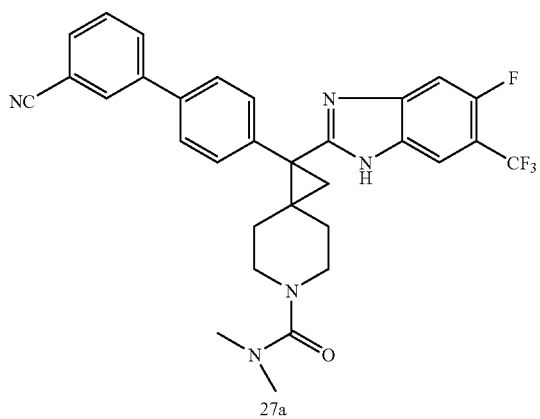

27a

To a flask containing 0.065 g of 4'-[1-(5-flouro-6-trifluoromethyl-1H-benzoimidazol-2-yl)-6-aza-spiro[2.5]oct-1-yl]-biphenyl-3-carbonitrile dihydrochloride were added a few milliliters of dichloromethane and 1N NaOH. The reaction was stirred at room temperature for about an hour. The aqueous and organic layers were separated and the organic layer was dried over MgSO$_4$ and concentrated. The yellow solid was taken up in 2 mL of dichloromethane and 0.025 mL of triethylamine followed by 0.020 mL of dimethylcarbamyl chloride. The reaction was stirred overnight under N$_2$. The reaction was washed with water, extracted with dichloromethane, dried over MgSO$_4$ and concentrated on silica gel. It was eluted with 2.5% methanol in dichloromethane to give 0.031 g of 27a as an orange foam. m/z calculated for $C_{31}H_{28}F_4N_5O^+$=562, found m/z=562 (m+H)$^+$ The following compounds were prepared analogously.

| Compound | Structure | Formula (M + 1) | MS Calcd | (MH+) Found |
|---|---|---|---|---|
| 27b | 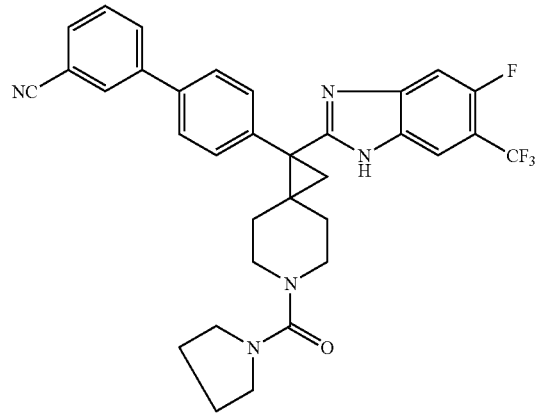 | $C_{33}H_{29}F_4N_5O.H^+$ | 588 | 588 |
| 27c | 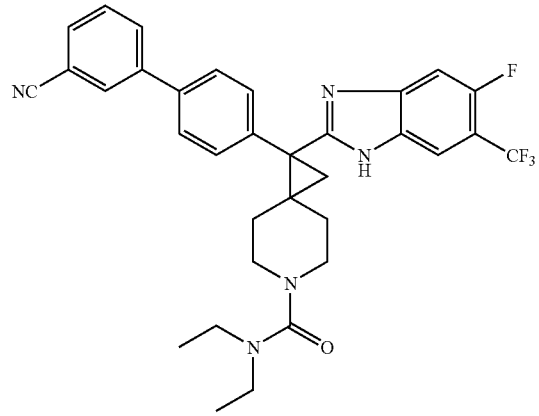 | $C_{33}H_{31}F_4N_5O.H^+$ | 590 | 590 |

-continued
| Compound | Structure | Formula (M + 1) | MS Calcd | (MH+) Found |
|---|---|---|---|---|
| 1x | 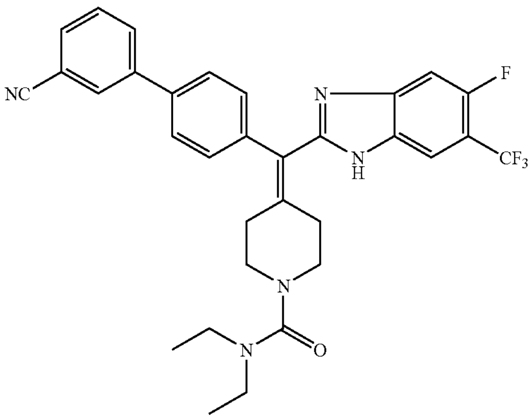 | $C_{32}H_{29}F_4N_5O.H^+$ | 576 | 576 |
| 1y | 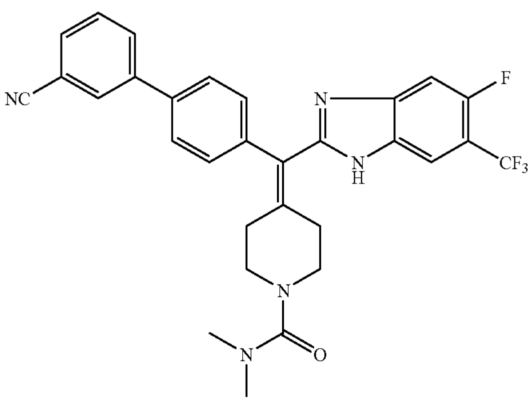 | $C_{30}H_{25}F_4N_5O.H^+$ | 548 | 548 |
Procedure T
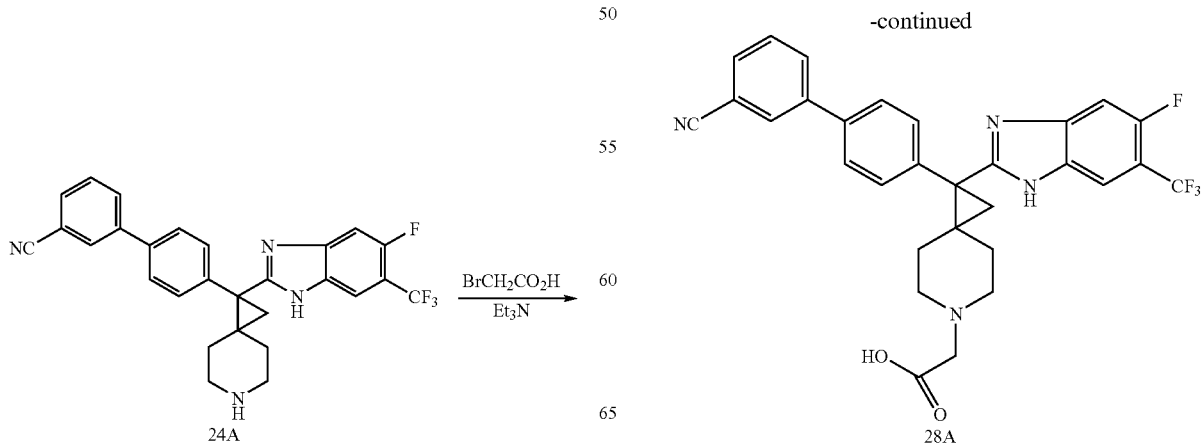

To a flask containing 0.065 g of 4'-[1-(5-flouro-6-trifluoromethyl-1H-benzoimidazol-2-yl)-6-aza-spiro[2.5]oct-1-yl]-biphenyl-3-carbonitrile dihydrochloride were added a few milliliters of dichloromethane and 1N NaOH. The reaction was stirred at room temperature for about an hour. The aqueous and organic layers were separated and the organic layer was dried over MgSO$_4$ and concentrated. The yellow solid was taken up in 2 mL of dichloromethane and 0.025 mL of triethylamine followed by 0.0149 g of bromoacetic acid. The reaction was stirred overnight under N$_2$. The reaction was washed with water, extracted with dichloromethane, dried over MgSO$_4$ and concentrated on silica gel. It was purified via reverse phase HPLC to give 0.0034 g of 28A as a white solid: m/z: calculated for $C_{30}H_{25}F_4N_4O_2^+$=549.2, found: 549.1 (m+H)$^+$ The following compound was prepared analogously.

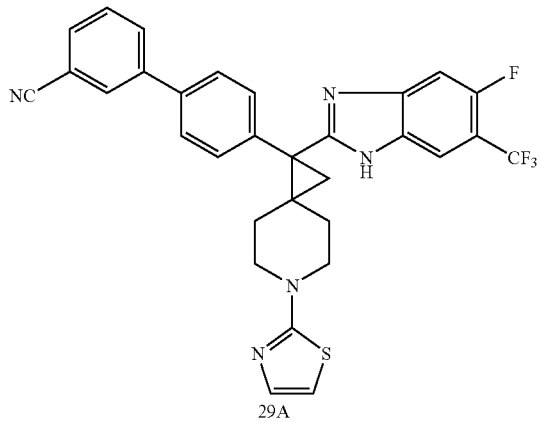

29A

| Compound | Structure | Formula (M + 1) | MS (MH+) Calcd | Found |
|---|---|---|---|---|
| 1z | 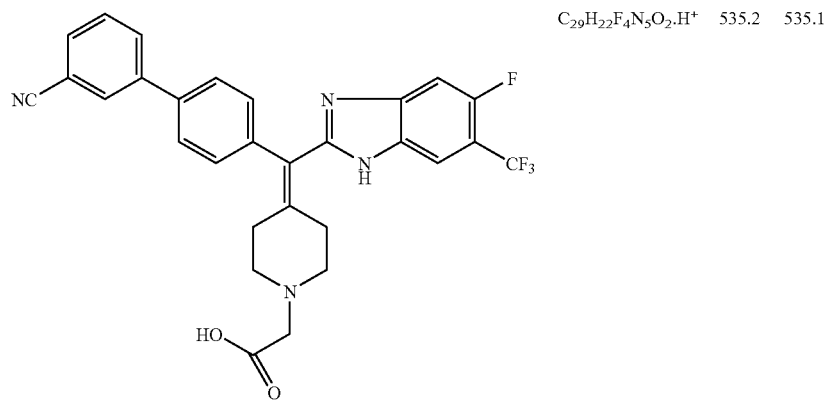 | $C_{29}H_{22}F_4N_5O_2 \cdot H^+$ | 535.2 | 535.1 |

Procedure U

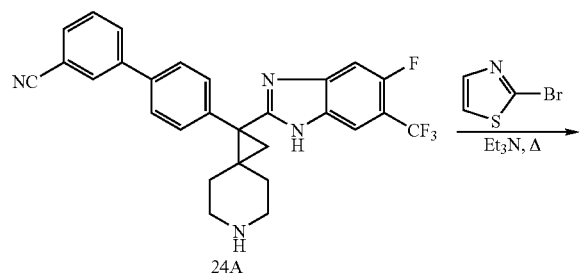

To a flask containing 0.061 g of 4'-[1-(5-Flouro-6-trifluoromethyl-1H-benzoimidazol-2-yl)-6-aza-spiro[2.5]oct-1-yl]-biphenyl-3-carbonitrile were added 2 mL of THF followed by 0.025 mL of Et$_3$N and 0.012 mL of 2-bromothiazole. The reaction was heated to reflux overnight. It was then cooled to room temperature, quenched with water, extracted with ethyl acetate, dried over MgSO4 and concentrated. It was purified via reverse phase HPLC to give a 0.0042 g of 29A as a white foam: m/z calculated for $C_{31}H_{23}F_4N_5S^+$=574.2, found: 574.1 (m+H)$^+$ The following compounds were prepared analogously.

| Compound | Structure | Formula (M + 1) | MS Calcd | (MH+) Found |
|---|---|---|---|---|
| 29b | 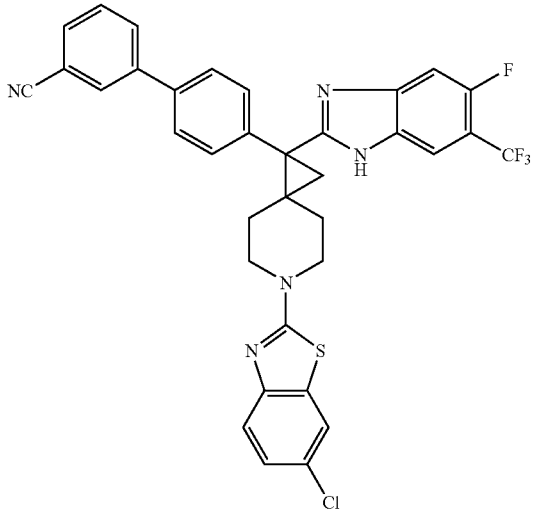 | $C_{35}H_{23}ClF_4N_5S.H^+$ | 658.1 | 658.1 |
| 29c | 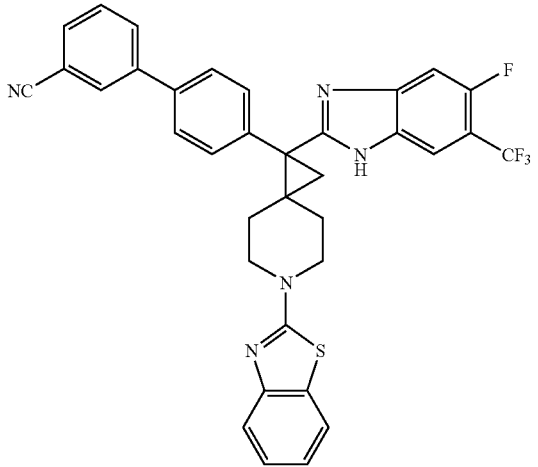 | $C_{35}H_{24}F_4N_5S.H^+$ | 624.2 | 624.2 |

MCH Receptor Binding Assay:

Membranes from CHO cells expressing the MCH receptor were prepared by lysing cells with 5 mM HEPES for 15 min at 4 C. Cell lysates were centrifuged (12.5000×g, 15 min) and the pellet was resuspended in 5 mM HEPES. For each 96-well plate (Microlite, Dynex Technologies), 1 mg of cell membranes were incubated with 10 mg of wheat germ agglutinin SPA beads (Amersham) for 5 min at 4 C in a volume of 10 ml of binding buffer (25 mM HEPES, 10 mM $MGCl_2$, 10 mM NaCl, 5 mM $MnCl_2$, 0.1% BSA). The membrane/bead mixture was centrifuged (1500×g, 3.5 min), the supernatant was aspirated, and the pellet was resuspended in 10 ml binding buffer. The centrifugation, aspiration and resuspension were then repeated. The membrane/bead mixture (100 μl) was then added to 96-well plates containing 50 μl of 500 pM [$^{125}$I]-MCH (NEN) and 50 ml of the appropriate concentration of compound (4× the desired final concentration). Nonspecific binding was determined by including 1 μM MCH in the binding reaction. The binding reaction was incubated at room temperature for 2 h. Plates were then analyzed in a TOPCOUNT microplate scintillation counter (Packard). Data was analyzed and Ki values were determined using GraphPad Prism.

Compounds with Ki values greater than 100 nM are designated in the table below as D class compounds.

Compounds with Ki values between 50 and 100 nM are designated in the table below as C class compounds.

Compounds with Ki values between 20 and 50 nM are designated in the table below as B class compounds.

Compounds with Ki values less than 20 nM are designated in the table below as A class compounds.

In a preferred embodiment of the invention, Example is, a Ki value of 3.5 nM was observed.

In another preferred embodiment of the invention, Example 24a, a Ki value of 1.7 nM was observed.

| Ex # or Cpd # | MCH Ki (nM) |
| --- | --- |
| 1a | D |
| 1b | A |
| 1c | A |
| 1d | A |
| 1e | B |
| 1f | A |
| 1g | C |
| 1h | D |
| 1i | D |
| 1j | C |
| 1k | B |
| 1l | B |
| 1m | C |
| 1n | D |
| 1o | C |
| 1p | D |
| 1q | C |
| 1r | A |
| 1s | A |
| 1t | D |
| 1u | C |
| 1v | C |
| 1w | D |
| 1x | B |
| 1y | B |
| 1z | A |
| 1aa | D |
| 1ab | D |
| 23a | D |
| 23b | D |
| 23c | A |
| 24a | A |
| 24b | A |
| 25a | A |
| 25b | A |
| 25c | A |
| 26a | C |
| 26b | D |
| 27a | B |
| 27b | B |
| 27c | D |
| 28a | B |
| 29a | D |
| 29b | D |
| 29c | D |

What is claimed is:

1. A compound represented by the structural formula

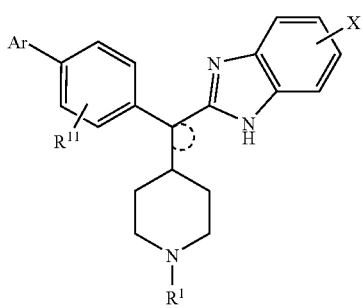

formula I or a pharmaceutically acceptable salt or solvate thereof, wherein the dashed line of

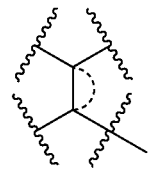

along with the adjoining single bond, together represent a double bond, a cyclopropyl or cyclobutyl;

Ar is aryl, heteroaryl, $R^4$-substituted aryl or $R^4$-substituted heteroaryl;

$R^1$ is hydrogen, alkyl, aralkyl, aryl, cycloalkyl, cycloalkylalkyl, heteroaralkyl, heteroaryl, $R^4$-substituted aralkyl, $R^4$-substituted aryl, $R^4$-substituted cycloalkyl, $R^4$-substituted cycloalkylalkyl, $R^4$-substituted heteroaralkyl, $R^4$-substituted heteroaryl, -alkylenyl-C(O)$R^8$, —C(O)$R^2$, —S(O$_2$)$R^7$, —S(O$_2$)N$R^2R^3$, —C(O)N$R^2R^3$ or —C(O)O$R^7$;

$R^2$ is hydrogen, heteroaryl, alkyl or aryl;

$R^3$ is hydrogen, heteroaryl, alkyl or aryl, where $R^2$ and $R^3$ can be optionally joined together and with the nitrogen to which they are attached, form a heterocyclyl ring, wherein said heterocyclyl ring can be optionally substituted with a ring system substituent, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halogen, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH (alkyl), $Y_1Y_2$N—, $Y_1Y_2$N-alkyl-, $Y_1Y_2$NC(O)—, $Y_1Y_2$NSO$_2$— and —SO$_2$N$Y_1Y_2$, wherein $Y_1$ and $Y_2$ can be the same or different and are independently selected from the group consisting of hydrogen, alkyl, aryl, cycloalkyl, and aralkyl;

$R^4$ is 1 to 5 moieties and each $R^4$ is independently selected from group the consisting of hydrogen, heterocyclyl, $R^8$-substituted heterocyclyl, heterocyclylalkyl, $R^8$-substituted heterocyclylalkyl, aryl, cycloalkyl, cycloalkylalkyl, heteroaralkyl, heteroaryl, $R^8$-substituted aryl, $R^8$-substituted cycloalkyl, $R^8$-substituted cycloalkylalkyl, $R^8$-substituted heteroaralkyl, $R^8$-substituted heteroaryl, —OH, alkoxy, —OCF$_3$, —CN, alkyl, halogen, —N$R^5R^6$, —N$R^5$C(O)$R^7$, —C(O)N$R^5R^6$, —N$R^5$S(O$_2$)$R^7$, —S(O$_2$)N$R^5R^6$, —S(O$_2$)$R^7$, —C(O)$R^7$, —C(O)O$R^5$, —CF$_3$, -alkyleneN$R^5R^6$, -alkyleneN$R^6$C(O)$R^7$, -alkyleneN$R^6$S(O$_2$)$R^7$, alkenyl, —N$R^5$C(O)N$R^5R^6$, -alkyleneN$R^5$C(O)O$R^7$, CHO and —C=NO$R^5$;

$R^5$ is hydrogen or alkyl;

$R^6$ is hydrogen, alkyl, aryl, aralkyl, heteroaryl or heteroaralkyl;

$R^7$ is alkyl, aryl, aralkyl, heteroaryl or heteroaralkyl;

$R^8$ is alkyl, —OH or hydroxyalkyl;

$R^{11}$ is 1 to 4 moieties and each $R^{11}$ is independently selected from group the consisting of hydrogen, alkoxy, alkyl, halogen, —OH, —OCF$_3$, CN and —CF$_3$; and X is 1 to 4 moieties and each X is independently selected from hydrogen, alkyl, aryl, cycloalkyl, heteroaryl, heterocyclyl, halogen, $R^4$-substituted aryl, $R^4$-substituted cycloalklyl, $R^4$-substituted heteroaryl, $R^4$-substituted heterocyclyl, —CF$_3$, —OCF$_3$, —OR$^2$, —CN, —C(O)R$^2$, —S(O$_2$)R$^7$, —C(O)NR$^5$R$^6$, —C(O)OR$^7$ and —NR$^5$C(O)R$^7$.

2. The compound of claim 1 wherein Ar is aryl, heteroaryl or $R^4$-substituted aryl.

3. The compound of claim 1 wherein $R^1$ is hydrogen, alkyl, aryl, cycloalkylalkyl, cycloalkyl, heteroaryl, $R^4$-substituted heteroaryl, -alkylenyl-C(O)R$^8$, —C(O)NR$^2$R$^3$, —C(O)OR$^7$ or —S(O$_2$)R$^7$.

4. The compound of claim 3 wherein $R^2$ and $R^3$ are ethyl or methyl or $R^2$ and $R^3$ are joined together and with the nitrogen to which they are attached, form a heterocyclyl ring of formula

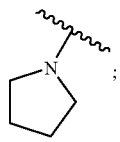

and
$R^7$ is methyl or —CH(CH$_3$)$_2$.

5. The compound of claim 1 wherein $R^7$ is methyl or —CH(CH$_3$)$_2$.

6. The compound of claim 1 wherein $R^4$ is 1 or 2 moieties, each $R^4$ is independently selected from the group consisting of hydrogen, heterocyclylalkyl, —CN, halogen, —NR$^5$R$^6$, —CF$_3$, -alkyleneNR$^5$R$^6$,

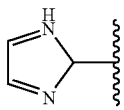

and CHO.

7. The compound of claim 1 wherein
Ar is aryl, heteroaryl or $R^4$-substituted aryl;
$R^1$ is hydrogen, alkyl, aryl, cycloalkylalkyl, cycloalkyl, heteroaryl, $R^4$-substituted heteroaryl, -alkylenyl-C(O)R$^8$, —C(O)NR$^2$R$^3$, —C(O)OR$^7$ or —S(O$_2$)R$^7$;
$R^2$ and $R^3$ are alkyl or $R^2$ and $R^3$ are joined together and with the nitrogen to which they are attached, form a heterocyclyl ring;
$R^4$ is 1 or 2 moieties, each $R^4$ is independently selected from the group consisting of hydrogen, heterocyclylalkyl, —CN, halogen, —NR$^5$R$^6$, —CF$_3$, -alkyleneNR$^5$R$^6$,

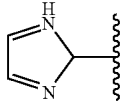

and CHO;
$R^5$ and $R^6$ are alkyl;
$R^7$ is methyl or —CH(CH$_3$)$_2$; and
X is 1 or 2 moieties and X is halogen or —CF$_3$.

8. The compound of claim 7 wherein
Ar is heteroaryl or $R^4$-substituted aryl;
$R^1$ is hydrogen, alkyl, aryl, cycloalkylalkyl, cycloalkyl, heteroaryl, $R^4$-substituted heteroaryl, -alkylenyl-C(O)R$^8$, —C(O)NR$^2$R$^3$, —C(O)OR$^7$ or —S(O$_2$)R$^7$;
$R^2$ and $R^3$ are alkyl or $R^2$ and $R^3$ are joined together and with the nitrogen to which they are attached, form a heterocyclyl ring;
$R^4$ is 1 or 2 moieties, each $R^4$ is independently selected from the group consisting of hydrogen, heterocyclylalkyl, —CN, -alkyleneNR$^5$R$^6$,

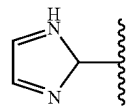

and CHO;
$R^5$ and $R^6$ are alkyl;
$R^7$ is methyl or —CH(CH$_3$)$_2$; and
X is 1 or 2 moieties and X is chloro, fluoro or —CF$_3$.

9. The compound of claim 8 wherein
Ar is

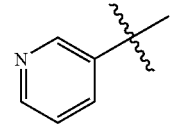

or $R^4$-substituted phenyl;
$R^1$ is hydrogen, methyl, benzyl, cyclopropylmethyl, cyclopropyl,

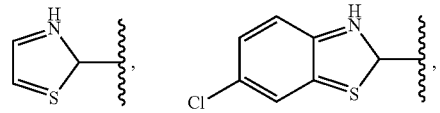

-alkylenyl-C(O)R$^8$, —C(O)NR$^2$R$^3$, —C(O)OR$^7$ or —S(O$_2$)R$^7$;
$R^2$ and $R^3$ are methyl or ethyl or $R^2$ and $R^3$ are joined together and with the nitrogen to which they are attached, form a heterocyclyl ring of formula

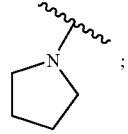

$R^4$ is 1 or 2 moieties, each $R^4$ is independently selected from the group consisting of hydrogen,

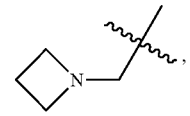

—CN, -methyleneNR$^5$R$^6$,

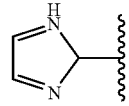

and CHO;
$R^5$ and $R^6$ are methyl;
$R^7$ is methyl or —CH(CH$_3$)$_2$;
$R^8$ is —OH; and
X is 2 moieties and X is chloro, fluoro or —CF$_3$.

10. The compound of claim 9 wherein Ar is

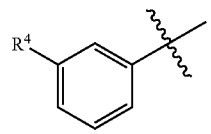

11. The compound of claim 10 wherein $R^4$ is independently selected from the group consisting of hydrogen,

—CN, -methyleneNR$^5$R$^6$,

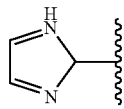

and CHO.

12. The compound of claim 1 wherein $R^{11}$ is hydrogen, alkoxy or —OH.

13. The compound of claim 1 wherein $R^{11}$ is methoxy.

14. The compound of claim 7 wherein X is substituted on the parent ring as follows

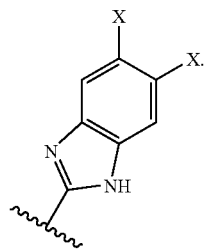

15. The compound of claim 1 wherein X is fluoro, chloro or —CF$_3$.

16. The compound of claim 1 wherein dashed line portion of formula I, as represented by

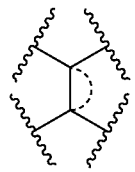

along with the accompanying single bond, together represent

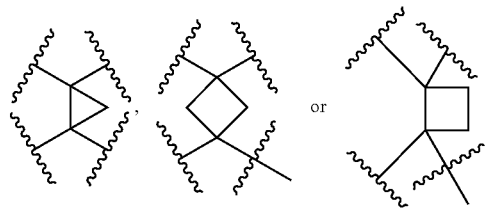

17. The compound of claim 1 wherein the dashed line of

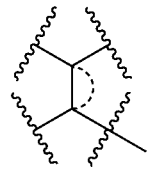

along with the adjoining single bond, together represent a double bond;
Ar is heteroaryl or R$^4$-substituted aryl;
R$^1$ is hydrogen, alkyl, aryl, cycloalkylalkyl, cycloalkyl, heteroaryl, R$^4$-substituted heteroaryl, -alkylenyl-C(O)R$^8$, —C(O)NR$^2$R$^3$, —C(O)OR$^7$ or —S(O$_2$)R$^7$;
R$^2$ and R$^3$ are alkyl or R$^2$ and R$^3$ are joined together and with the nitrogen to which they are attached, form a heterocyclyl ring;
R$^4$ is 1 or 2 moieties, each R$^4$ is independently selected from the group consisting of hydrogen, heterocyclylalkyl, —CN, halogen, —NR$^5$R$^6$, —CF$_3$, -alkyleneNR$^5$R$^6$,

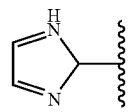

and CHO;
R$^5$ is hydrogen or alkyl;
R$^6$ is hydrogen, alkyl, aryl, aralkyl, heteroaryl or heteroaralkyl;
R$^7$ is alkyl, aryl, aralkyl, heteroaryl or heteroaralkyl;
R$^8$ is alkyl, —OH or hydroxyalkyl;
R$^{11}$ is hydrogen, alkoxy or —OH; and
X is 1 to 4 moieties and each X is independently selected from hydrogen, halogen and —CF$_3$.

18. The compound of claim 1 wherein the dashed line of

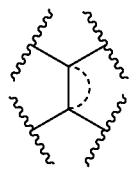

along with the adjoining single bond, together represent a cyclopropyl of formula

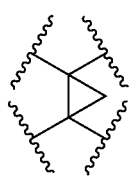

Ar is heteroaryl or R$^4$-substituted aryl;
R$^1$ is hydrogen, alkyl, aryl, cycloalkylalkyl, cycloalkyl, heteroaryl, R$^4$-substituted heteroaryl, -alkylenyl-C(O)R$^8$, —C(O)NR$^2$R$^3$, —C(O)OR$^7$ or —S(O$_2$)R$^7$;

R² and R³ are alkyl or R² and R³ are joined together and with the nitrogen to which they are attached, form a heterocyclyl ring;

R⁴ is 1 or 2 moieties, each R⁴ is independently selected from the group consisting of hydrogen, heterocyclylalkyl, —CN, halogen, —NR⁵R⁶, —CF₃, -alkyleneNR⁵R⁶,

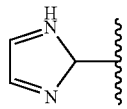

and CHO;

R⁵ is hydrogen or alkyl;
R⁶ is hydrogen, alkyl, aryl, aralkyl, heteroaryl or heteroaralkyl;
R⁷ is alkyl, aryl, aralkyl, heteroaryl or heteroaralkyl;
R⁸ is alkyl, —OH or hydroxyalkyl;
R¹¹ is hydrogen, alkoxy or —OH; and
X is 1 to 4 moieties and each X is independently selected from hydrogen, halogen and —CF₃.

19. A compound of formula I selected from the group consisting of

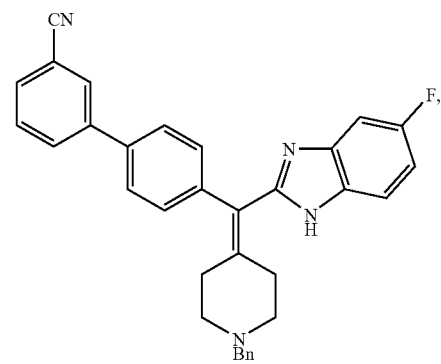

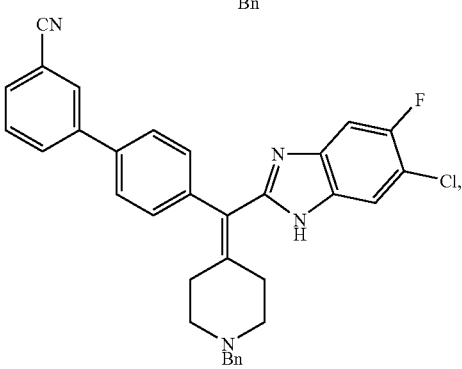

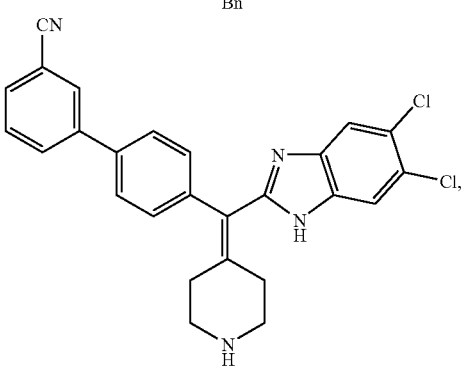

-continued

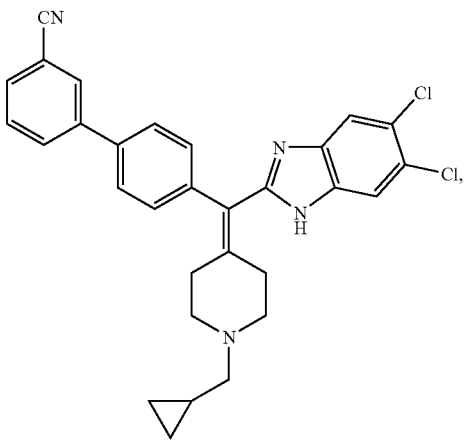

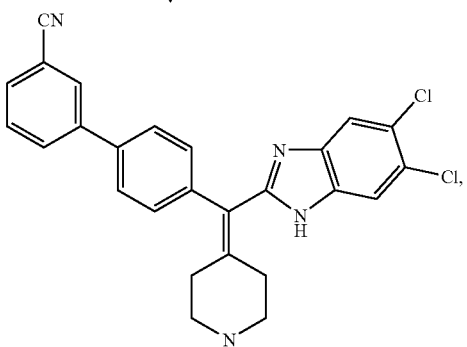

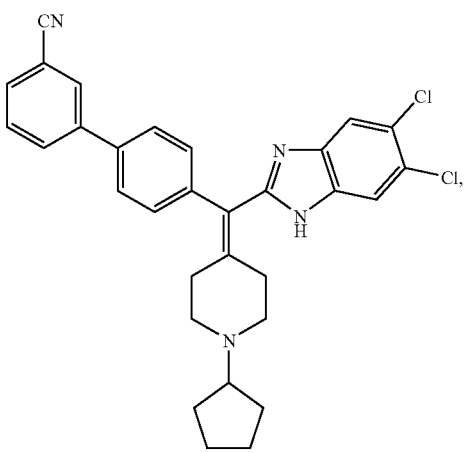

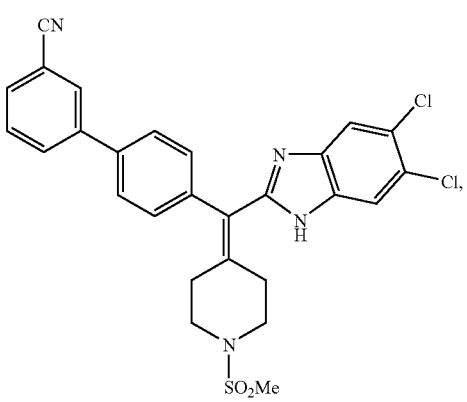

-continued
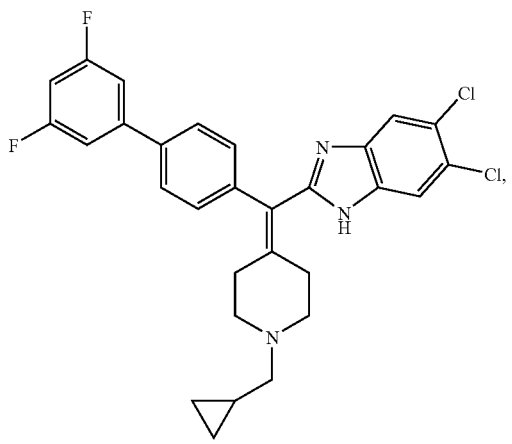
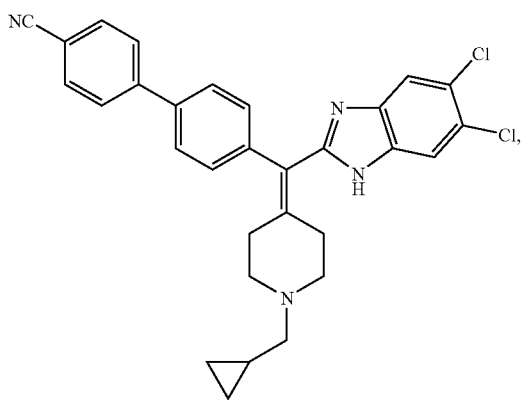
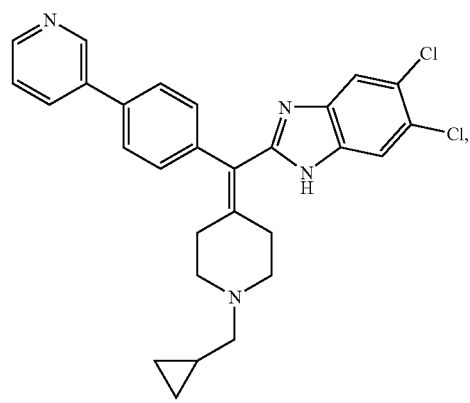
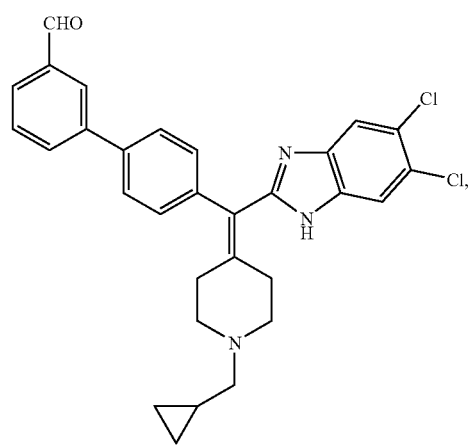
-continued
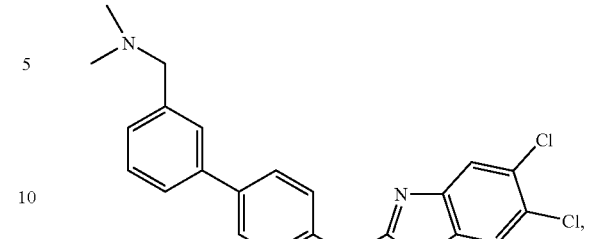
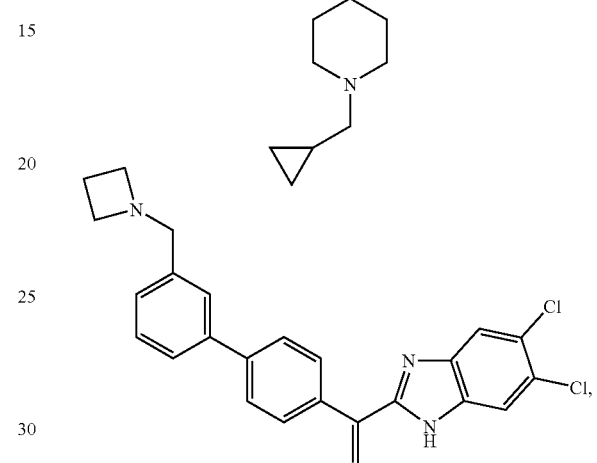
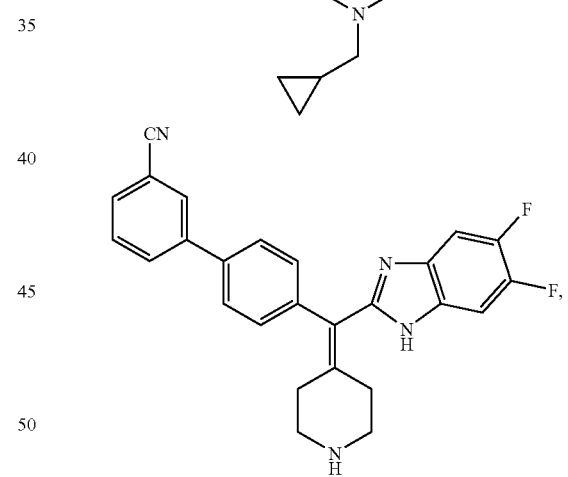
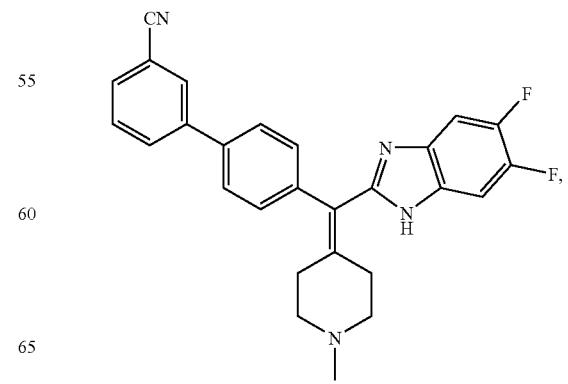

81
-continued
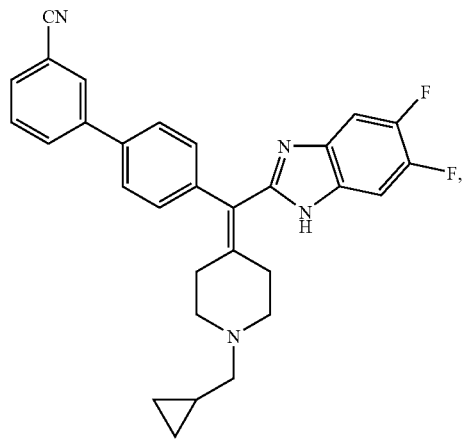
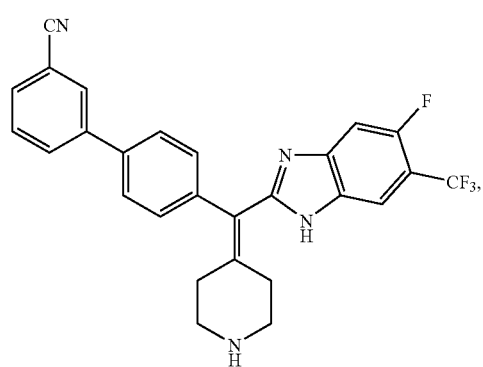
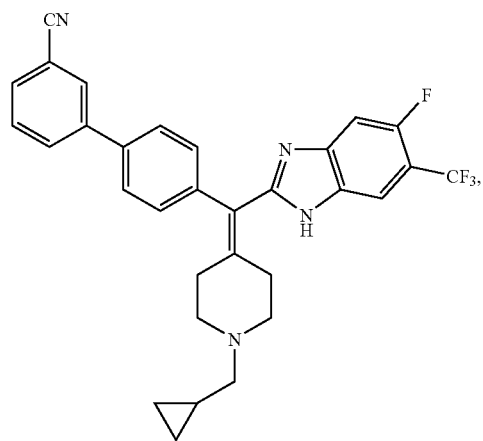
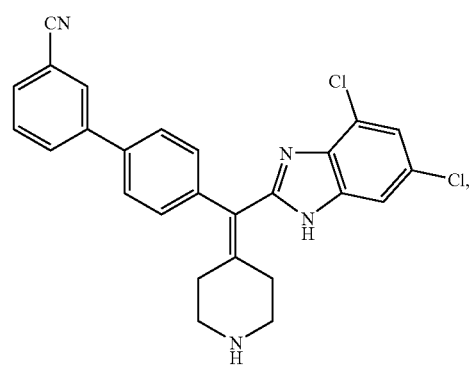
82
-continued
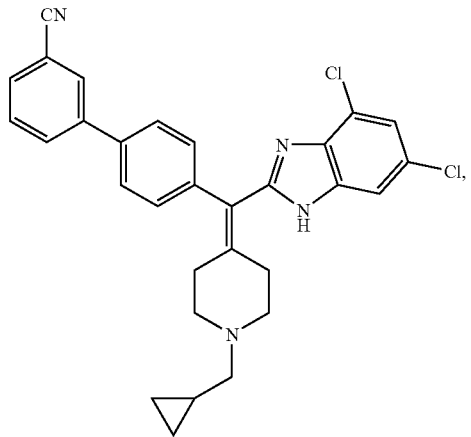
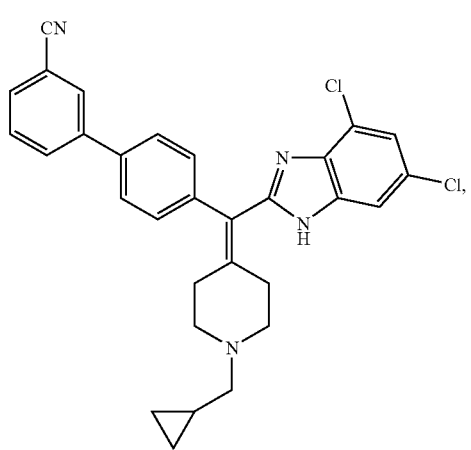
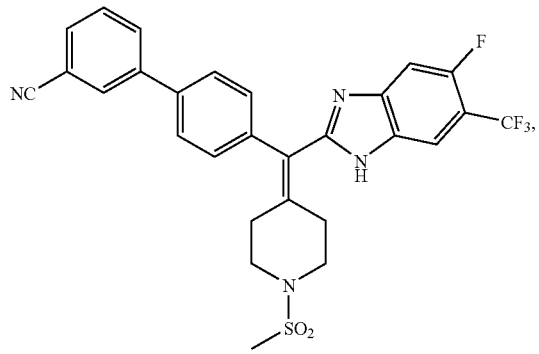
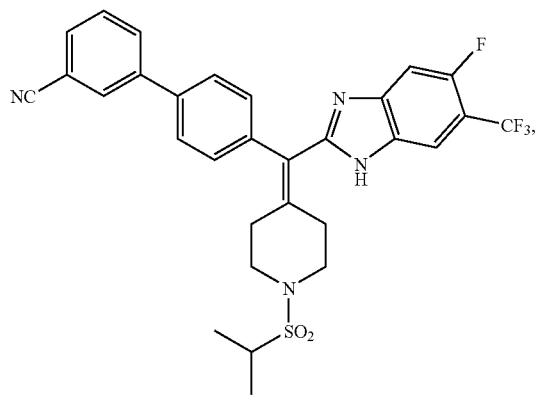

83
-continued
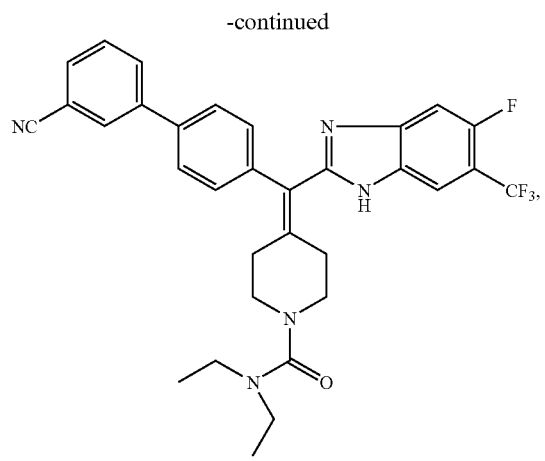
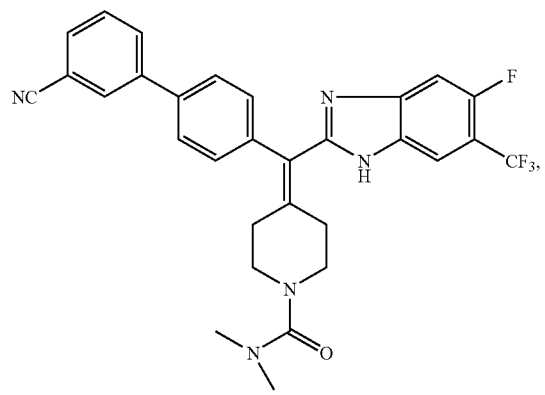
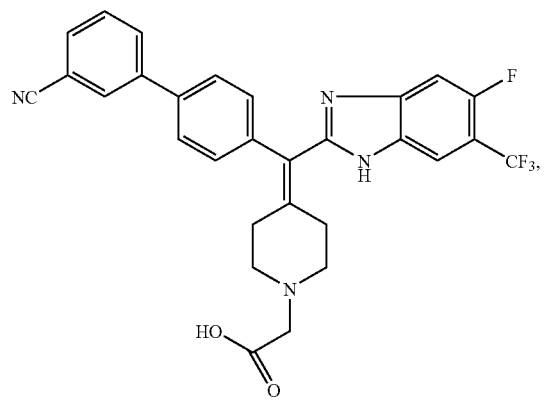
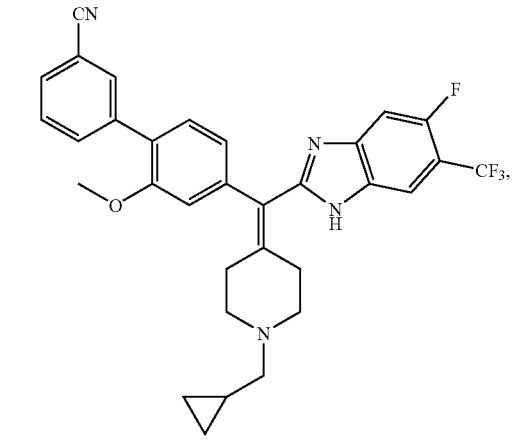
84
-continued
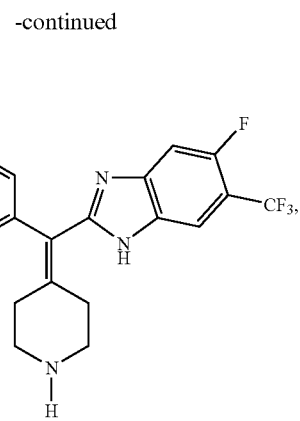
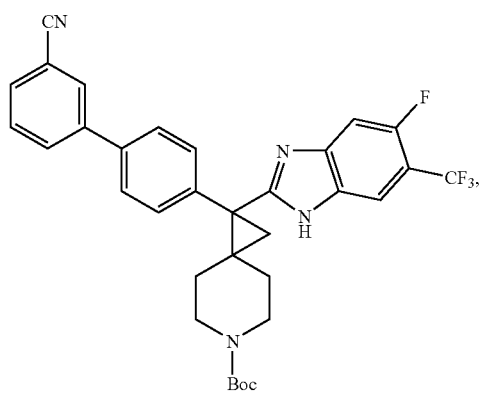
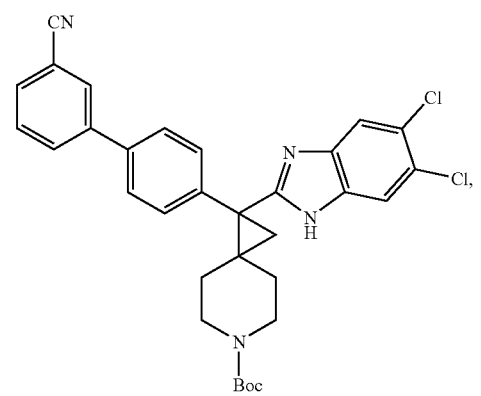
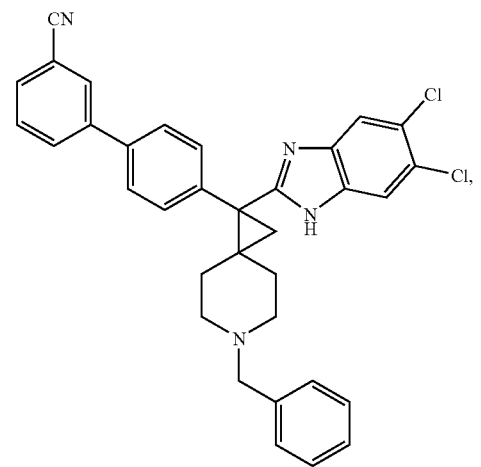

-continued
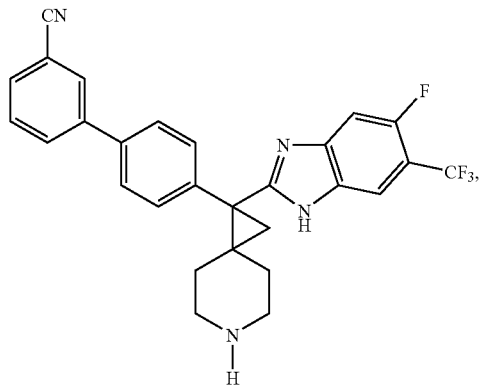
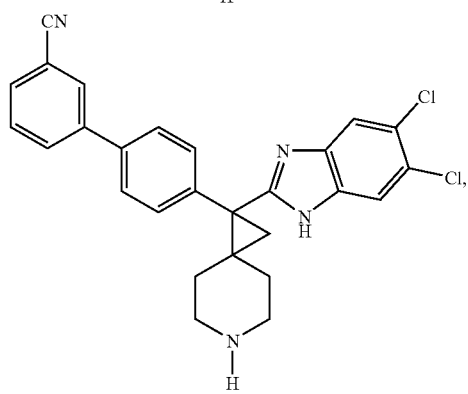
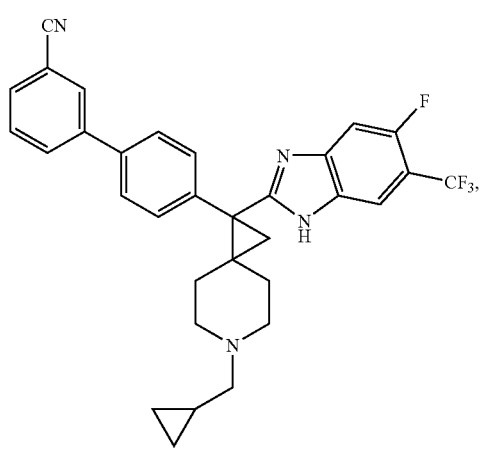
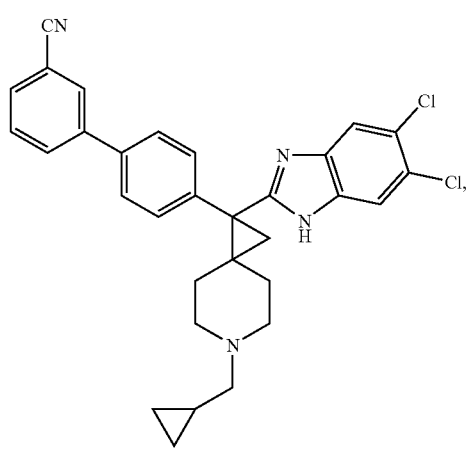
-continued
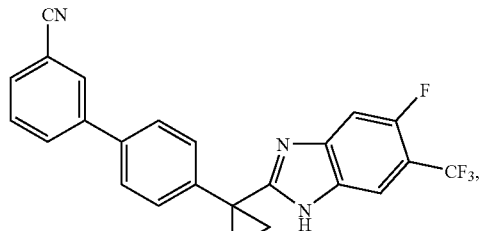
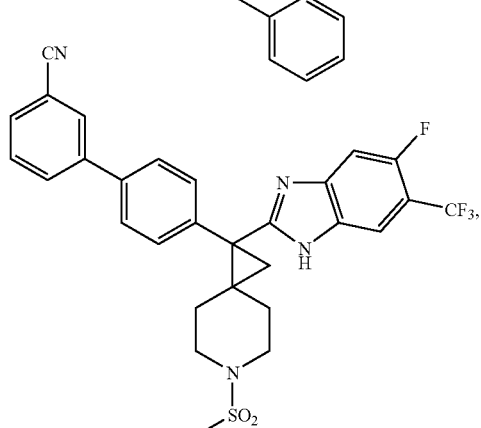
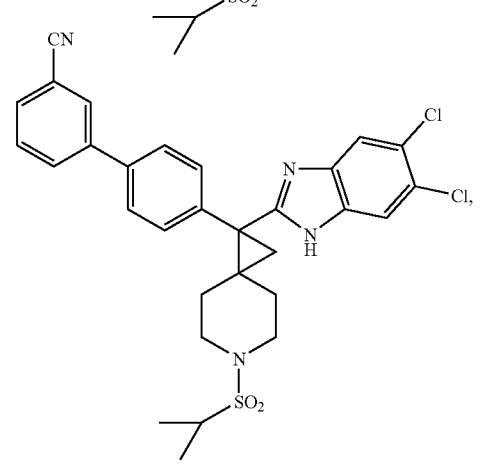
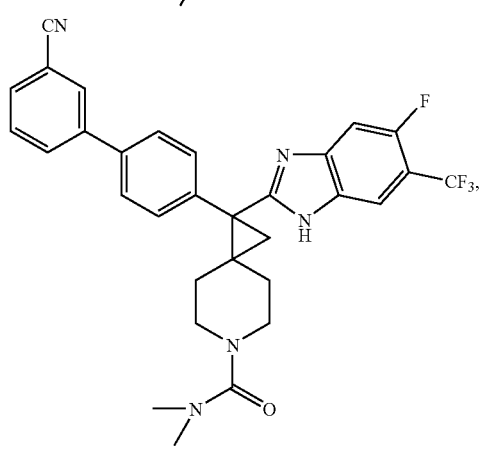

-continued

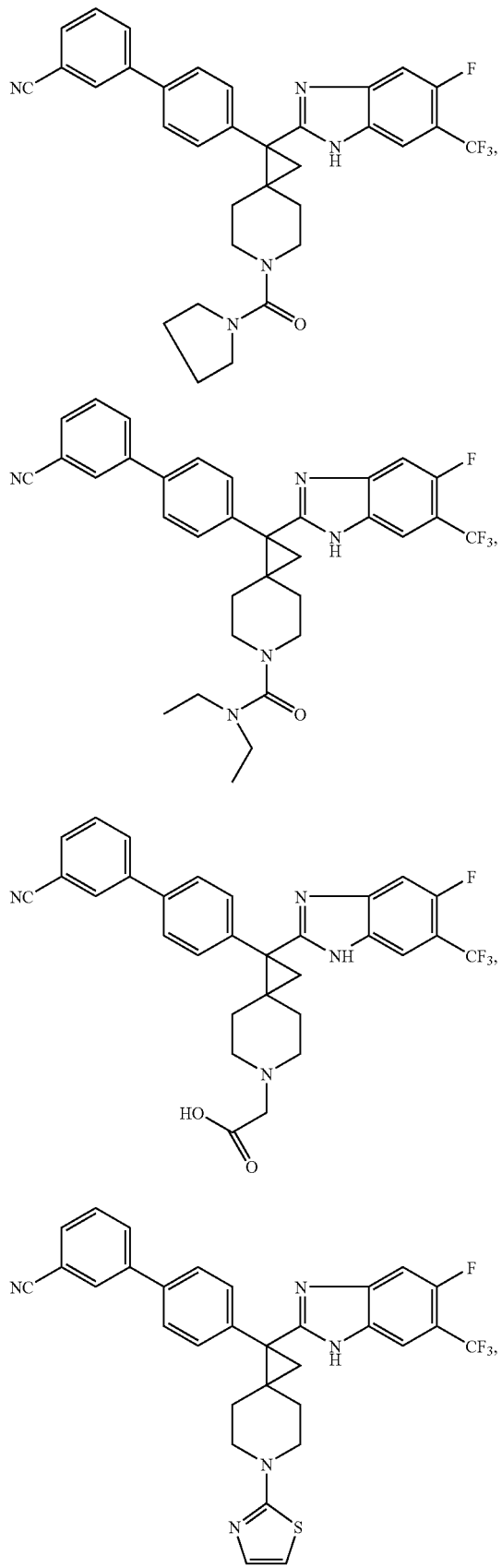

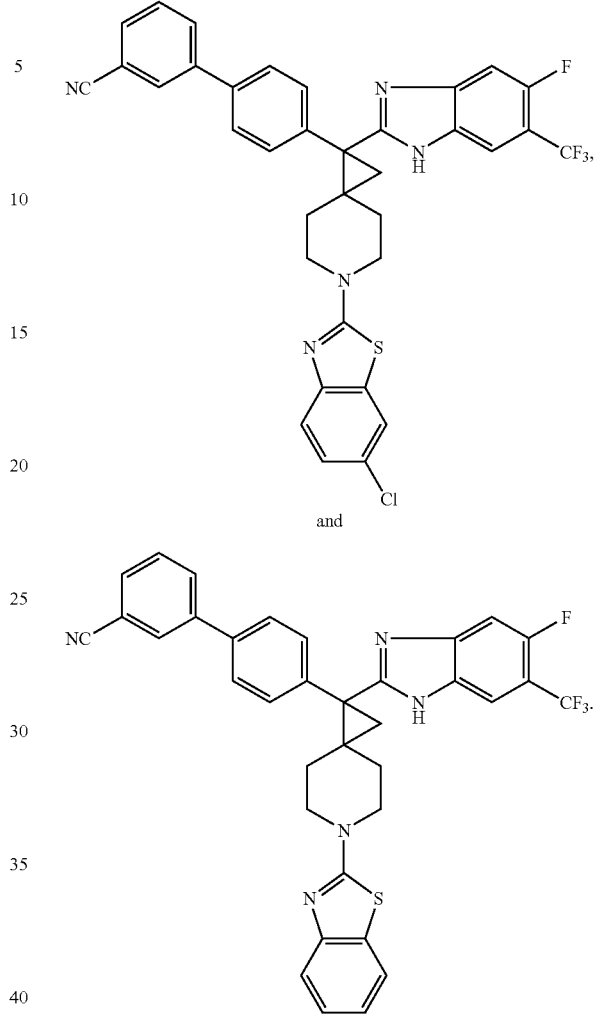

20. A method of treating obesity or hyperphagia comprising administering to a patient a therapeutically effective amount of at least one compound of claim 1 to a patient in need of such treatment.

21. A method of treating obesity or hyperphagia comprising administering to a patient a therapeutically effective amount of at least one compound of claim 19 to a patient in need of such treatment.

22. A pharmaceutical composition comprising a therapeutically effective amount of at least one compound of claim 1 in combination with at least one pharmaceutically acceptable carrier.

23. A pharmaceutical composition comprising a therapeutically effective amount of at least one compound of claim 19 in combination with at least one pharmaceutically acceptable carrier.

24. A process for making a pharmaceutical composition comprising combining at least one compound of claim 1, and at least one pharmaceutically acceptable carrier.

25. A process for making a pharmaceutical composition comprising combining at least one compound of claim 19, and at least one pharmaceutically acceptable carrier.

* * * * *